United States Patent [19]

Devore et al.

[11] Patent Number: 5,539,068

[45] Date of Patent: Jul. 23, 1996

[54] GROUP 4, METAL-CONJUGATED DIENE METALLOCYCLOPENTENE COMPLEXES, AND ADDITION POLYMERIZATION CATALYSTS THEREFROM

[75] Inventors: David D. Devore, Midland, Mich.; James C. Stevens, Richmond, Tex.; Francis J. Timmers, Midland, Mich.; Robert K. Rosen, Sugar Land, Tex.

[73] Assignee: The Dow Chemical Company, Midland, Mich.

[21] Appl. No.: 429,974

[22] Filed: Apr. 27, 1995

Related U.S. Application Data

[62] Division of Ser. No. 267,993, Jun. 28, 1994, Pat. No. 5,486,632.

[51] Int. Cl.$^6$ ..................... C08F 4/643
[52] U.S. Cl. .......... 526/126; 526/127; 526/133; 526/134; 526/160; 526/170; 526/352; 502/103; 502/117; 502/152; 556/7; 556/11; 556/22; 556/52
[58] Field of Search .............. 526/126, 127, 526/133, 134, 160, 170; 502/103, 117, 128, 152, 153; 556/7, 11, 52

[56] References Cited

U.S. PATENT DOCUMENTS

| 5,055,438 | 10/1991 | Canich | 502/117 |
|---|---|---|---|
| 5,057,475 | 10/1991 | Canich et al. | 502/104 |
| 5,064,802 | 11/1991 | Stevens et al. | 502/155 |
| 5,096,867 | 3/1992 | Canich | 502/103 |
| 5,132,380 | 7/1992 | Stevens et al. | 526/126 |
| 5,153,157 | 10/1992 | Hlatky et al. | 502/117 |
| 5,198,401 | 3/1993 | Turner et al. | 502/155 |
| 5,321,106 | 6/1994 | La Pointe et al. | 526/126 |
| 5,350,723 | 9/1994 | Niethamer et al. | 502/104 |
| 5,374,696 | 12/1994 | Rosen et al. | 526/126 |
| 5,399,635 | 3/1995 | Neithamer et al. | 526/126 |

FOREIGN PATENT DOCUMENTS

| 277003 | 1/1988 | European Pat. Off. . |
|---|---|---|
| 416815 | 8/1990 | European Pat. Off. . |
| 468651 | 7/1991 | European Pat. Off. . |
| 514828 | 5/1992 | European Pat. Off. . |
| 520732 | 11/1992 | European Pat. Off. . |
| WO92/00333 | 1/1992 | WIPO . |
| 93/19104 | 3/1993 | WIPO . |
| 93/23412 | 11/1993 | WIPO . |
| W094/00500 | 1/1994 | WIPO . |
| W094/07930 | 4/1994 | WIPO . |

OTHER PUBLICATIONS

Erker et al., Angew Chem., Int., Ed. Eng. 23,455–456 (1984).
C. Kruger, et al., Organometallics, 4, 215–223 (1985).
G. Stout, et al., X–ray Structure Determination, A Practical Guide, Macmillan Co., pp. 430–431 (1968).
Yasuda, et al., Organometallics, 1, 388 (1982).
Yasuda, et al., Acc. Chem. Res. 18, 120 (1985).
Erker, et al., Adv. Organomet. Chem., 24, 1 (1985).
Yamamoto et al., Organometallics, 8, 105 (1989).
Blenkers, J., et al., Organometallics, 6, 459 (1987).

*Primary Examiner*—Mark Nagumo

[57] ABSTRACT

Novel Group 4 metal complexes containing one and only one cyclic delocalized, anionic, π-bonded group wherein the metal is in the +4 formal oxidation state and having a bridged ligand structure, also referred to as constrained geometry complexes and a conjugated diene divalent anionic ligand group; catalytic derivatives of such complexes including novel zwiterionic complexes; and the use thereof as catalysts for polymerizing olefins, diolefins and/or acetylenically unsaturated monomers.

11 Claims, 1 Drawing Sheet

GROUP 4, METAL-CONJUGATED DIENE METALLOCYCLOPENTENE COMPLEXES, AND ADDITION POLYMERIZATION CATALYSTS THEREFROM

CROSS-REFERENCE TO RELATED APPLICATION

This is a divisional of application Ser. No. 08/267,993 filed Jun. 28, 1994, now U.S. Pat. No. 5,486,632.

BACKGROUND OF THE INVENTION

This invention relates to certain Group 4 metal complexes comprising a single, cyclic, delocalized π-bonded ligand group wherein the metal of said complexes is in the +4 formal oxidation state. More particularly, this invention relates to such complexes wherein the metal is covalently bonded to the cyclic group via the delocalized π-system and also covalently bonded thereto via a divalent ligand group. Such complexes are referred to in the art as "constrained geometry" complexes. The invention further relates to techniques for preparing such complexes, to derivatives of such complexes that are catalysts useful for polymerizing olefins, diolefins and/or acetylenically unsaturated monomers, as well as such polymerization processes.

The preparation and characterization of certain biscyclopentadienyl zirconium and hafnium diene complexes are described in the following references: Yasuda, et al., *Organometallics*, 1,388 (1982), (Yasuda I); Yasuda, et al. *Acc. Chem. Res.*, 18, 120 (1985), (Yasuda I); Erker, et al., *Adv. Organomet. Chem.*, 24, 1 (1985) Erker, et al. (I); and U.S. Pat. No. A 5,198,401. The latter reference describes the use of Cp$_2$Zr(diene) as an olefin polymerization catalyst in combination with ammonium borate cocatalysts.

The preparation of certain Ti, Zr, and Hf monocyclopentadienyl diene complexes lacking the present bridged ligand structure, was described in Yamamoto et al., *Organometallics*, 8, 105 (1989) (Yamamoto) and Blenkers, J, et al., *Organometallics*, 6, 459 (1987). Only the Hf complexes disclosed in the latter reference were described as having utility as catalyst components.

Constrained geometry metal complexes, including titanium complexes, and methods for their preparation are disclosed in U.S. application Ser. No. 545,403, filed Jul. 3, 1990 (EP-A-416,815), pending; U.S. application Ser. No. 547,718, filed July 3, 1990 (EP-A-468,651) abandoned; U.S. application Ser. No. 702,475, filed May 20, 1991 (EP-A-514,828) abandoned; U.S. application Ser. No. 876,268, filed May 1, 1992, (EP-A-520,732) pending and U.S. application Ser. No. 8,003, filed Jan. 21, 1993 (WO93/19104) now U.S. Pat. No. 5,374,696, to Rosen et al., as well as U.S. Pat. No. A 5,055,438, U.S. Pat. No. A 5,057,475, U.S. Pat. No. A 5,096,867, U.S. Pat. No. A 5,064,802 and U.S. Pat. No. A5, 132,380. The teachings of all the foregoing patents, publications and patent applications is hereby incorporated by reference.

Despite the advance in the art brought about by the foregoing constrained geometry complexes, new and improved catalytic compounds are still desired.

SUMMARY OF THE INVENTION

Figure 1:
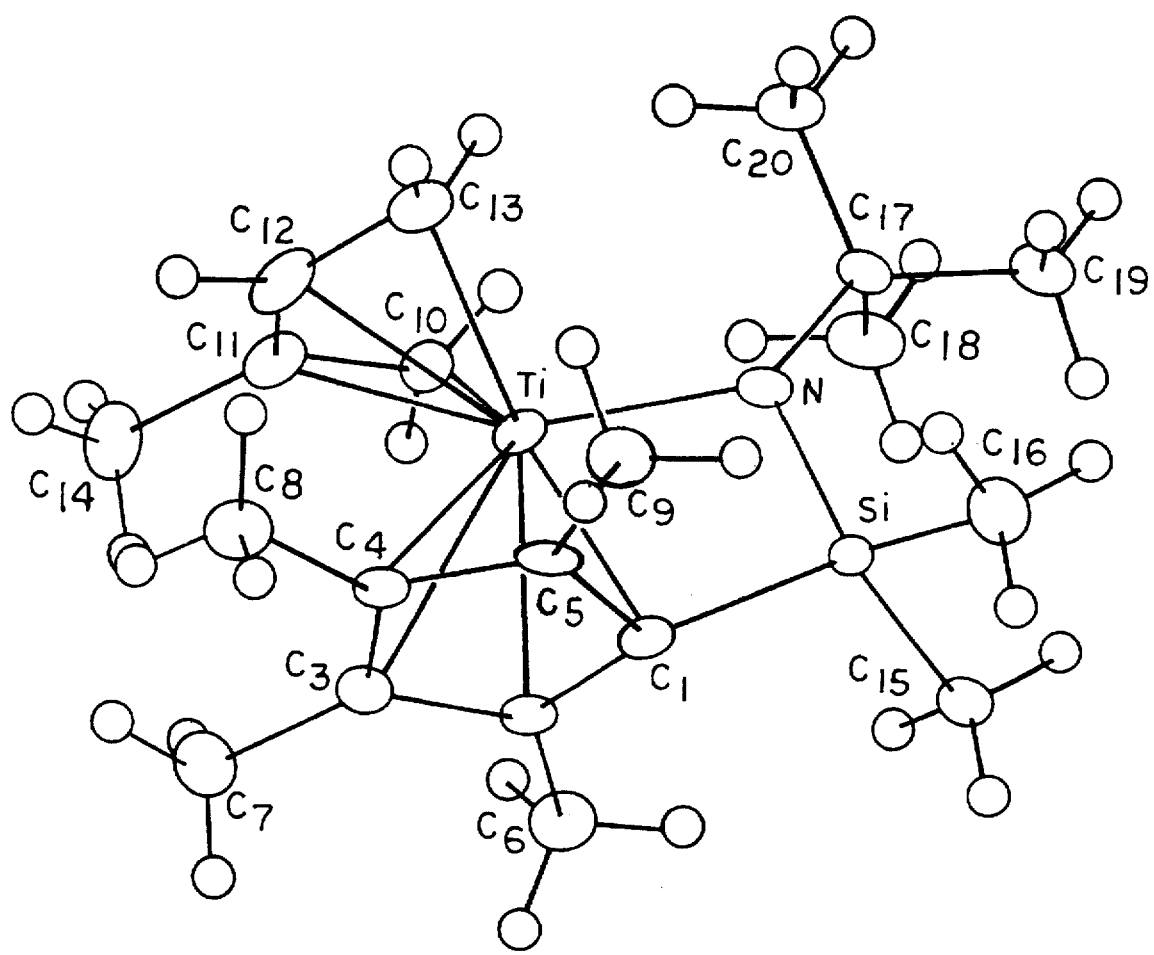
FIG. 1 is the molecular structure of the composition of Example 2 as determined by X-ray crystal structure analysis.

According to the present invention there are provided metal complexes containing one and only one cyclic, delocalized, anionic, π-bonded group, said complexes corresponding to the formula:

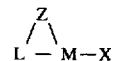

wherein:

M is a Group 4 metal in the +4 formal oxidation state;

L is a group containing a cyclic, delocalized, anionic, π-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 nonhydrogen atoms; and X is a conjugated diene or a hydrocarbyl-, halocarbyl-, or silyl-substituted derivative thereof, said X having from 4 to 40 nonhydrogen atoms, and being coordinated to M so as to form a metallocyclopentene therewith.

Additionally according to the present invention there is provided a process for preparing a metal complex containing one and only one cyclic, delocalized π-bonded group, said complex corresponding to the formula:

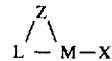

wherein M, L, Z and X are as previously defined, comprising:

contacting a compound according to the formula M(X*)$_2$ or a solvated adduct thereof wherein X* is halo and M is as previously defined, with a source of a dianion ligand, (Z-L)$^{-2}$, a conjugated diene compound corresponding to X, and an alkali metal hydrocarbyl- or alkaline earth metal hydrocarbyl compound of up to 10 carbons in an inert diluent. Alternatively, the metal halide, MX*$_4$ or MX*$_3$, or solvated adduct thereof, and dianion ligand precursor may be prereacted under diGrignard addition reaction conditions to give the precursor, M(-Z-L-)(X)$_1$ or M(-Z-L-)(X)$_2$ which is then reacted with the conjugated diene compound and alkali metal hydrocarbyl- or alkaline earth metal hydrocarbyl compound. The Group 4 metal compound(s), s conjugated diene and alkali metal hydrocarbyl- or alkaline earth metal hydrocarbyl compound may be combined in any order.

Further according to the present invention there are provided catalysts for polymerization of addition polymerizable monomers comprising a combination of one or more of the above metal complexes and one or more activating cocatalysts or activating techniques.

The present invention also provides a polymerization process comprising contacting one or more addition polymerizable monomers with a catalyst comprising one or more of the above metal complexes and one or more activating cocatalysts or activating techniques. The polymerization may be s performed under solution, suspension, slurry, or gas phase process conditions, and the catalyst or individual components thereof may be used in a heterogeneous, ie. a supported state, or in a homogeneous state as dictated by process conditions. The catalyst can be used in combination with one or more additional catalysts of the same or different nature either simultaneously in the same reactor or sequentially in separate reactors.

Finally, the complexes resulting from activation by combination with neutral Lewis acid activating cocatalysts are novel compositions of matter corresponding to the formula:

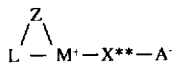

wherein:

M is a Group 4 metal in the +4-formal oxidation state;

L is a group containing a cyclic, delocalized, anionic, π-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 nonhydrogen atoms;

X** is the divalent remnant of the conjugated diene, X, formed by ring opening at one of the carbon to metal bonds of the metallocyclopentene; and A− is the moiety derived from the activating cocatalyst.

Catalysts prepared from the complexes of the present invention possess improved catalytic properties compared to corresponding complexes lacking in a σ-bound diene substituent. Surprisingly, the present complexes are s more efficient catalysts and possess desirable operating features, particularly when activated by strong Lewis acid cocatalysts.

DETAILED DESCRIPTION

All reference to the Periodic Table of the Elements herein shall refer to the Periodic Table of the Elements, published and copyrighted by CRC Press, Inc., 1989. Also, any reference to a Group or Groups shall be to the Group or Groups as reflected in this Periodic Table of the Elements using the IUPAC system for numbering groups.

The diene group desirably does not decompose under reaction conditions used to prepare the complexes of the invention. Under subsequent polymerization conditions, or in the formation of catalytic derivatives of the present complexes, the diene group may undergo chemical reactions or be replaced by another ligand.

The present complexes contain a diene ligand which is coordinated formally as a metallacycle containing σ-bonds (σ-bound diene) where the metal is in the +4 formal oxidation state. Such Group 4 metal σ-bound diene complexes have a structure which is formally a metallocyclopentene wherein the bonding between the metal and the diene can be described as a divalent 2-butene- 1,4-diyl σ-bonded to a tetravalent metal, optionally containing a single π-bond involving the π electrons between internal carbons of the conjugated diene. Such structures are depicted as structure A and Structure 13 as follows:

A

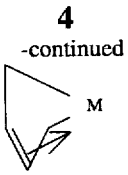

B

The nomenclature for such σ-bound diene complexes can be either as a metallocyclopentene (referring to the compounds as 2-butene-1,4-diyl compounds) or generically as the parent diene, ie. butadiene. Those of skill in the art will recognize the interchangability of these names. For example, the prior art biscyclopentadienyl zirconium complex containing a σ-bound 2,3-dimethyl- 1,4-butadiene group would be named either bis-cyclopentadienyl 2-butene- 2,3-dimethyl-1,4-diyl zirconium or bis-cyclopentadienyl 2,3-dimethyl- 1,4-butadiene zirconium.

The presence of such σ-bound diene is readily determined by X-ray crystallography or by NMR spectral characterization according to the techniques of Yasuda I, Yasuda II, and Erker, et al., Supra, as well as the references cited therein. The present complexes are to be contrasted with other diene containing complexes wherein the diene forms a π-complex. By the term "π-complex" is meant both the donation and back acceptance of electron density by the ligand are accomplished using ligand π-orbitals, i.e., the diene is π-bound (π-bound diene).

A suitable method of determining the existence of a σ-complex in conjugated diene containing metal complexes is the measurement of metalcarbon atomic spacings for the carbons of the conjugated diene using common X-ray crystal analysis techniques. Measurements of atomic spacings between the metal and C1, C2, C3, C4 (M-C1, M-C2, M-C3, M-C4, respectively) (where C1 and C4 are the terminal carbons of the 4 carbon conjugated diene group and C2 and C3 are the internal carbons of the of the 4 carbon conjugated diene group) may be made. If the difference between these bond distances, Δd, using the following formula:

$$\Delta d = \left[ \left\{ \frac{(M-C1)+(M-C4)}{2} \right\} - \left\{ \frac{(M-C2)+(M-C3)}{2} \right\} \right]$$

is less than −0.15Å, the diene is considered to form a σ-complex with M, ie., a σ-bound diene.

Examples wherein the above method for determination of π-complexes and σ-complexes has been applied to prior art compounds are found in Erker, et al (I), Angew. Chem, Int. Ed., Eng., 23,455-456 (1984) (Erker et al. (II)) and Yamamoto, Supra. In the former reference (η³-allyl)(η⁴-butadiene)(η⁵-cyclopentadienyl)zirconium was crystallographically characterized. The M-C1 and M-C4 distances were both 2.360 (±0.005) Å. The M-C2 and M-C3 distances were both 2.463 (±0.005) Å, giving a Δd of −0.103Å. In the latter reference (η⁵-pentamethylcyclopentadienyl)(η⁴-1,4-diphenyl-1,3 -butadiene)titanium chloride was shown to have M-C1 and M-C4 distances of 2.233 (±0.006) Å. The M-C2 and M-C3 distances were both 2.293 (±0.005) Å, giving a Δd of −0.060Å. Accordingly, these complexes contains π-bound dienes and the metals are in the +2 formal oxidation state. Erker et al. (I) also disclosed bis(cyclopentadienyl)zirconium (2,3-dimethyl-1,3-butadiene). In this complex the M-C1 and M-C4 distances were 2.300 Å. The M-C2 and M-C3 distances were both 2.597 Å, giving a Δd of −0.297Å. Accordingly, this complex contains a σ-bound diene and the zirconium is in the +4 formal oxidation state. In the use of such X-ray crystal analysis techniques at least "good" and preferably "excellent" determination quality as defined by G. Stout et al., *X-ray Structure Determination, A Practical Guide*, Macmillan Co., pg 430–431, (1968) is used.

Alternatively, complexes of the present invention wherein X is a conjugated diene in the form of a σ-complex and M is in the +4 formal oxidation state are identified using nuclear magnetic resonance spectroscopy techniques. The teachings of Erker, et al. (I), C. Krüger, et al. Organometallics, 4, 215–223, (1985), and Yasuda I, disclose these well known techniques for distinguishing between π-bound diene complexes and σ-bound diene complexes. The teachings of the foregoing references related to σ-bound diene complexes is hereby incorporated by reference.

When the foregoing techniques are indeterminate of the existence of σ-complexes, the relevant atomic spacings may be determinable by a restricted Hartree-Fock method, which is a standard method of molecular orbital (MO) theory, as explained hereinafter.

Not withstanding the foregoing statement, it is to be understood that the present complexes may be formed and utilized as a mixture with a corresponding π-bound diene complex so long as the complexes of the present invention are present in a molar amount from greater than 90 up to 100 percent, more preferably in a molar amount from 91 to 100 percent, most preferably in a molar amount from 95 to 100 percent, based on the total amount of complexes present. Techniques for separation and purification of σ-bound diene complexes from mixtures of π-bound diene complexes and σ-bound diene complexes are known in the art and disclosed for example in the previously mentioned Yasuda I, Yasuda II, and Erker, et al. references and may be employed if desired to prepare and isolate the complexes in greater purity.

Inasmuch as the complexes can contain only one cyclic delocalized, anionic, π-bonded group, it follows that Z or the diene, singly or in combination, cannot comprise a cyclopentadienyl group or other cyclic, anionic delocalized π-bonded group.

Preferred metal complexes according to the present invention correspond to the formula:

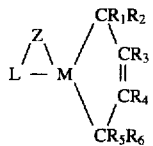

wherein:

M is titanium or zirconium in the +4 formal oxidation state;

L is a group containing a cyclic, delocalized, anionic, π-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 nonhydrogen atoms; and $R_1$, $R_2$, $R_3$, $R_4$, $R_5$, and $R_6$ are independently hydrogen or a substituent selected from the group consisting of hydrocarbyl, silyl and combinations thereof, said substituent having from 1 to 20 nonhydrogen atoms.

Further preferred metal coordination complexes according to the present invention correspond to the formula:

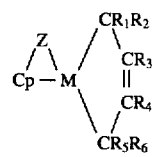

wherein Z, and M are as previously defined;

each $R_1$, $R_2$, $R_3$, $R_4$, $R_5$, and $R_6$ is independently hydrogen or a substituent selected from the group consisting of hydrocarbyl, silyl and combinations thereof, said substituent having from 1 to 10 nonhydrogen atoms; and Cp is a $C_5H_4$ cyclopentadienyl group bound to Z and bound in an $\eta^5$ bonding mode to M or is such an $\eta^5$ bound group substituted with from one to four substituents independently selected from hydrocarbyl, halocarbyl, silyl, germyl, halo, cyano, and combinations thereof, said substituent having up to 20 nonhydrogen atoms, and optionally, two such substituents (except cyano or halo) together cause Cp to have a fused ring structure.

More preferred metal coordination complexes according to the present invention correspond to the formula:

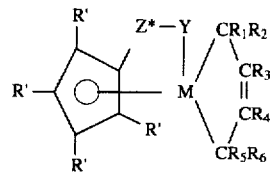

wherein:

R' each occurrence is independently selected from hydrogen, hydrocarbyl, silyl, germyl, halo, cyano, and combinations thereof, said R' having up to 20 nonhydrogen atoms, and optionally, two R' groups (where R' is not hydrogen, halo or cyano) together form a divalent derivative thereof connected to adjacent positions of the cyclopentadienyl ring to form a fused ring structure;

Y is —O—, —S—, —NR*—, —PR*—;

M is titanium or zirconium in the +4 formal oxidation state;

each $R_1$, $R_2$, $R_3$, $R_4$, $R_5$, and $R_6$ is independently selected from the group consisting of hydrogen and $C_{1-8}$ hydrocarbyl; and Z* is SiR*$_2$, CR*$_2$, SiR*$_2$SiR*$_2$, CR*$_2$CR*$_2$, CR*=CR*, CR*$_2$SiR*$_2$, or GeR*$_2$; wherein:

R* each occurrence is independently hydrogen, or a member selected from hydrocarbyl, silyl, halogenated alkyl, halogenated aryl, and combinations thereof, said R* having up to 10 nonhydrogen atoms, and optionally, two R* groups from Z* (when R* is not hydrogen), or an R* group from Z* and an R* group from Y form a ring system.

Preferably, R' independently each occurrence is hydrogen, hydrocarbyl, silyl, halo and combinations thereof said R' having up to 10 nonhydrogen atoms, or two R' groups (when R' is not hydrogen or halo) together form a divalent derivative thereof; most preferably, R' is hydrogen, methyl, ethyl, propyl, butyl, pentyl, hexyl, (including where appropriate all isomers), cyclopentyl, cyclohexyl, norbornyl, benzyl, or phenyl or two R' groups (except hydrogen) are linked together, the entire $C_5R'_4$ group thereby being, for example, an indenyl, tetrahydroindenyl, fluorenyl, tetrahydrofluorenyl, or octahydrofluorenyl group.

Further preferably, at least one of R' or R* is an electron donating moiety. By the term "electron donating" is meant that the moiety is more electron donating than hydrogen. Thus, highly preferably Y is a nitrogen or phosphorus containing group corresponding to the formula —N(R")— or —P(R")—, wherein R" is $C_{1-10}$ hydrocarbyl.

Examples of suitable dienes include butadiene, isoprene and especially internally substituted dienes such as 2,3-dimethylbutadiene and 2,3-diphenylbutadiene.

Most highly preferred metal coordination complexes are amidosilane- or amidoatkanediyl- compounds corresponding to the formula:

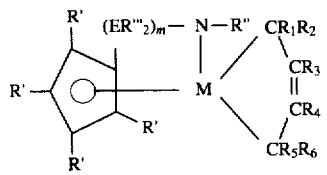

wherein:

M is titanium;

$R_1$, $R_2$, $R_5$, and $R_6$ are hydrogen;

$R_3$, and $R_4$ are hydrogen, $C_{1-4}$ alkyl or phenyl;

R' each occurrence is independently selected from hydrogen, silyl, hydrocarbyl and combinations thereof, said R' having up to 10 carbon or silicon atoms, or two such R' groups on the substituted cyclopentadienyl group (when R' is not hydrogen) together form a divalent derivative thereof connected to adjacent positions of the cyclopentadienyl ring;

R" is t-butyl;

R''' is independently each occurrence hydrogen or $C_{1-10}$ hydrocarbyl;

E is independently each occurrence silicon or carbon; and m is 1 or 2.

Examples of the metal complexes according to the present invention include compounds wherein $(ER'''_2)_m$ is dimethylsilanediyl, or ethanediyl; the cyclic delocalized π-bonded group is cyclopentadienyl, tetramethylcyclopentadienyl, indenyl, tetrahydroindenyl, fluorenyl, tetrahydrofluorenyl or octahydrofluorenyl; and the diene is isoprene or 2,3-dimethylbutadiene.

If the aforementioned empirical techniques for measuring whether a complex possesses the requisite diene σ-complex configuration are indeterminate, a restricted Hartree-Fock method may be utilized to determine molecular spacings. Such Hartree-Fock methods are well known having been disclosed by: W. J. Hehre, L. Radom, P. R. Schleyer, and J. A. Pople, *Ab Initio Molecular Orbital Theory* (Wiley, New York, 1986); K. D. Dobbs and W. J. Hehre, "Molecular Orbital Theory of the Properties of Inorganic and Organometallic Compounds, 5, Extended Basis Sets For First-row Transition Metals" [3-21G, 3-21G*, Sc-Zn], *J. Comput. Chem.* 8, 861 (1987); K. D. Dobbs and W. J. Hehre, Molecular Orbital Theory of the Properties of Inorganic and Organometallic Compounds, 5, Extended Basis Sets For First-row Transition Metals. [3-21G, 3- 21G*, Sc-Zn], *J. Comput. Chem.* 9,801 (1988) (Erratum to above); and K. D. Dobbs and W. J. Hehre, Molecular Orbital Theory of the Properties of Inorganic and Organometallic Compounds, 6, Extended Basis Sets for Second-row Transition Metals [3-21G, 3-21G*, Y-Cd], *J. Comput. Chem.* 8,880–93 (1987).

According to the technique as utilized herein, solutions to the quantum mechanical equations for the electronic structures of isolated molecules in the gas phase are solved according to the well known, rigorous, ab initio method, using a 3-21ddG basis set. The 3-21ddG basis set uses all of the functions from 3-21 G, and adds a diffuse d function to each transition metal atom, as disclosed by: P. J. Hay, Gaussian Basis Sets for Molecular Calculations, the Representation of 3d Orbitals in Transition-metal Atoms, [3-21ddG], *J. Chem. Phys.* 66, 4377–84 (1977); A. K. Rappe, T. A. Smedley, and W. A. Goddard, III, Flexible d Basis Sets for Scandium Through Copper [3-21ddG], *J. Phys. Chem.* 85,2607–11 (1981); and P. J. Hay and W. R. Wadt, Ab Initio Effective Core Potentials for Molecular Calculations, Potentials for the Transition Metal Atoms Scandium to Mercury, [3-21ddG], *J. Chem. Phys.* 82,270–83 (1985). For transition metals, it is well known that the diffuse d function improves the treatment of the various possible electronic configurations. The exponent of the added function is determined from the ratios of values for the other exponents. The diffuse d exponents added are: Ti, 0.101; Zr, 0.055.

The HF/3-21ddG calculations are carried out using GAUSSIAN 92™, Revision D.2, available from Gaussian, Inc., Carnegie Office Park, Building 6, Pittsburgh, Pa. 15106, or equivalent program. The technique is further disclosed in J. B. Foresman and A. Frisch, *Exploring Chemistry with Electronic Structure Methods: A Guide to Using Gaussian*, Gaussian, Inc., Pittsburgh, Pa., 1993. The teachings of all of the foregoing references related to molecular calculations is hereby incorporated by reference.

More particularly, the structure of a complex is calculated as follows:

1. An initial structure is constructed using a molecular modeling program such as POLYGRAF™ " Molecular Design and Analysis Program, version 3.21 (06101/93), available from Molecular Simulations, Inc., 16 New England Executive Park, Burlington, Mass. 01803-5297, or equivalent program.

2. Optimized structures are obtained by an iterative method using the GAUSSIAN™ 92 program, or subsequent versions thereof. In each optimization cycle, the energy and atomic forces (energy gradients) are used to generate a new, refined structure or atomic positions. The final optimized structure is obtained when the displacements and forces of all atoms meet convergence Thresh holds of 0.00180 atomic units and 0.00045 atomic units, respectively. At this point, the total energy is minimized with respect to all degrees of freedom (molecular structure variables). For nonlinear molecules, there are 3n-6 degrees of freedom, where n is the number of atoms. These 3n-6 degrees of freedom are expressed as a combination of atomic coordinates (x, y, z) and internal coordinates (bond lengths, bond angles, and torsion angles).

3. The total energies for various isomers calculated by HF/3-21ddG are then compared to determine the lowest energy isomer and the atomic coordinates for that isomer are selected for determination of atomic spacings, Ad, according to the previously disclosed formula.

For organometal compounds such as the present, the HF/3-2 1 ddG structures have been found to be accurate to better than 0.2/Å, 0.06 Å, 3°, and 5°, for the atomic positions, bond lengths, bond angles, and torsion angles, respectively, as compared to structures obtained by x-ray diffraction.

Specific metal complexes included within the present invention are:

(tert-butylamido)($\eta^5$-cyclopentadienyl)-1,2-ethanediyltitanium butadiene; (tert-butylamido)($\eta^5$-cyclopentadienyl)-1,2-ethanediyltitanium 2,3-dimethylbutadiene; (tert-butylamido)($\eta^5$-cyclopentadienyl)-1,2-ethanediyltitanium isoprene; (tert-butylamido)($\eta^5$-cyclopentadienyl)-1,2-ethanediyltitanium 2,3-bis(trimethylsilyl)butadiene; (tert-butylamido)($\eta^5$-cyclopentadienyl)-1,2-ethanediyltitanium 2,3-phenylbutadiene; (methylamido)($\eta^5$-cyclopentadienyl)-1,2-ethanediyltitanium butadiene; (methylamido)($\eta^5$-cyclopentadienyl)-1,2-ethanediyltitanium 2,3-dimethylbutadiene; (methylamido)($\eta^5$-cyclopentadienyl)-1,2-ethanediyltitanium isoprene; (methylamido)($\eta^5$-cyclopentadienyl)-1,2-ethanediyltitanium 2,3-bis(trimethylsilyl)butadiene; (methylamido)($\eta^5$-cyclopentadienyl)-1,2-ethanediyltitanium 2,3-diphenylbutadiene; (phenylamido)($\eta^5$-cyclopentadienyl)-1,2-ethanediyltitanium butadiene; (phenylamido)($\eta^5$-cyclopentadienyl)-1,2-ethanediyltitanium 2,3-dimethylbutadiene; (phenylamido)($\eta^5$-cyclopentadienyl)-1,2-ethanediyltitanium isoprene; (phenylamido)($\eta^5$-cyclopentadienyl)-1,2-ethanediyltitanium 2,3-bis(trimethylsilyl)butadiene; (phenylamido)($\eta^5$-cyclopentadienyl)-1,2-ethanediyltitanium 2,3-diphenylbutadiene; (cyclododecylamido)($\eta^5$-cyclopentadienyl)-1,2-ethanediyltitanium butadiene; (cyclododecylamido)($\eta^5$-cyclopentadienyl)-1,2-ethanediyltitanium 2,3-dimethylbutadiene; (cyclododecylamido)($\eta^5$-cyclopentadienyl)-1,2-ethanediyltitanium isoprene; (cyclododecylamido)($\eta^5$-cyclopentadienyl)-1,2-ethanediyltitanium 2,3-bis(trimethylsilyl)butadiene; (cyclododecylamido)($\eta^5$-cyclopentadienyl)-1,2-ethanediyltitanium 2,3-diphenylbutadiene; (phenylphosphido)($\eta^5$-cyclopentadienyl)-1,2-ethanediyltitanium butadiene; (phenylphoshido)($\eta^5$-cyclopentadienyl)-1,2-ethanediyltitanium 2,3-dimethytbutadiene; (phenylphosphido)($\eta^5$-cyclopentadienyl)-1,2-ethanediyltitanium isoprene; (phenylphosphido)($\eta^5$-cyclopentadienyl)-1,2-ethanediyltitanium 2,3-bis(trimethylsilyl)butadiene; (phenylphosphido)($\eta^5$-cyclopentadienyl)-1,2-ethanediyltitanium 2,3-diphenylbutadiene;

(tert-butylamido)(tetramethyl-$\eta^5$-cyclopentadienyl)-1,2-ethanediyltitanium butadiene; (tert-butylamido)(tetramethyl-$\eta^5$-cyclopentadienyl)-1,2-ethanediyltitanium 2,3-dimethylbutadiene; (tert-butylamido)(tetramethyl-$\eta^5$-cyclopentadienyl)-1,2-ethanediyltitanium isoprene; (tert-butylamido)(tetramethyl-$\eta^5$-cyclopentadienyl)-1,2-ethanediyltitanium 2,3-bis(trimethylsilyl)butadiene; (tert-butylamido)(tetramethyl-$\eta^5$-cyclopentadienyl)-1,2-ethanediyltitanium 2,3-diphenytbutadiene; (methylamido)(tetramethyl-$\eta^5$-cyclopentadienyl)-1,2-ethanediyltitanium butadiene; (methylamido)(tetramethyl-$\eta^5$-cyclopentadienyl)-1,2-ethanediyltitanium 2,3-dimethylbutadiene; (methylamido)(tetramethyl-$\eta^5$-cyclopentadienyl)-1,2-ethanediyltitanium isoprene; (methylamido)(tetramethyl-$\eta^5$-cyclopentadienyl)-1,2-ethanediyltitanium 2,3-bis(trimethylsilyl)butadiene; (methylamido)(tetramethyl-$\eta^5$-cyclopentadienyl)-1,2-ethanediyltitanium 2,3-diphenylbutadiene; (phenylamido)(tetramethyl-$\eta^5$-cyclopentadienyl)-1,2-ethanediyltitanium butadiene; (phenylamido)(tetramethyl-$\eta^5$-cyclopentadienyl)-1,2-ethanediyltitanium 2,3-dimethylbutadiene; (phenylamido)(tetramethylo-$\eta^5$-cyclopentadienyl)-1,2-ethanediyltitanium isoprene; (phenylamido)(tetramethyl-$\eta^5$-cyclopentadienyl)-1,2-ethanediyltitanium 2,3-bis(trimethylsilyl)butadiene; (phenylamido)(tetramethyl-$\eta^5$-cyclopentadienyl)-1,2-ethanediyltitanium 2,3-diphenylbutadiene; (cyclododecylamido)(tetramethyl-$\eta^5$-cyclopentadienyl)-1,2-ethanediyltitanium butadiene; (cyclododecylamido)(tetramethyl-$\eta^5$-cyclopentadienyl)-1,2-ethanediyltitanium 2,3-dimethylbutadiene; (cyclododecylamido)(tetramethyl-$\eta^5$-cyclopentadienyl)-1,2-ethanediyltitanium isoprene; (cyclododecylamido)(tetramethyl-$\eta^5$-cyclopentadienyl)-1,2-ethanediyltitanium 2,3-bis(trimethylsilyl)butadiene; (cyclododecylamido)(tetramethyl-$\eta^5$-cyclopentadienyl)-1,2-ethanediyltitanlum 2,3-diphenytbutadiene; (phenylphosphido)(tetramethyl-$\eta^5$-cyclopentadienyl)-1,2-ethanediyltitanium butadiene; (phenylphosphido)(tetramethyl-$\eta^5$-cyclopentadienyl)-1,2-ethanediyltitanium 2,3-dimethylbutadiene; (phenylphosphido)(tetramethyl-$\eta^5$-cyclopentadienyl)-1,2-ethanediyltitanium isoprene; (phenylphosphido)(tetramethyl-$\eta^5$-cyclopentadienyl)-1,2-ethanediyltitanium 2,3-bis(trimethylsilyl)butadiene; (phenylphosphido)(tetramethyl-$\eta^5$-cyclopentadienyl)-1,2-ethanediyltitanium 2,3-diphenylbutadiene;

(tert-butylamido)(t-butyl-$\eta^5$-cyclopentadienyl)-1,2-ethanediyltitanium butadiene; (tert-butylamido)(t-butyl-$\eta^5$-cyclopentadienyl)-1,2-ethanediyltitanium 2,3-dimethylbutadiene; (tert-butylamido)(t-butyl-$\eta^5$-cyclopentadienyl)-1,2-ethanediyltitanium isoprene; (tert-butylamido)(t-butyl-$\eta^5$-cyclopentadienyl)-1,2-ethanediyltitanium 2,3-bis(trimethylsilyl)butadiene; (methylamido)(t-butyl-$\eta^5$-cyclopentadienyl)-1,2-ethanediyltitanium butadiene; (tert-butylamido)(t-butyl-$\eta^5$-cyclopentadienyl)-1,2-ethanediyltitanium 2,3-diphenylbutadiene; (methylamido)(t-butyl-$\eta^5$-cyclopentadienyl)-1,2-ethanediyltitanium butadiene; (methylamido)(t-butyl-$\eta^5$-cyclopentadienyl)-1,2-ethanediyltitanium 2,3-dimethylbutadiene; (methylamido)(t-butyl-$\eta^5$-cyclopentadienyl)-1,2-ethanediyltitanium isoprene; (methylamido)(t-butyl-$\eta^5$-cyclopentadienyl)-1,2-ethanediyltitanium 2,3-bis(trimethylsilyl)butadiene; (methylamido)(t-butyl-$\eta^5$-cyclopentadienyl)-1,2-ethanediyltitanium 2,3-diphenylbutadiene; (phenylamido)(t-butyl-$\eta^5$-cyclopentadienyl)-1,2-ethanediyltitanium butadiene; (phenylamido)(t-butyl-$\eta^5$-cyclopentadienyl)-1,2-ethanediyltitanium 2,3-dimethylbutadiene; (phenylamido)(t-butyl-$\eta^5$-cyclolpentadienyl)-1,2-ethanediyltitanium isoprene; (phenylamido)(t-butyl-$\eta^5$-cyclopentadienyl)-1,2-ethanediyltitanium 2,3-bis(trimethylsilyl)butadiene; (phenylamido)(t-butyl-$\eta^5$-cyclopentadienyl)-1,2-ethanediyltitanium 2,3-diphenyt-butadiene; (cyclododecylamido)(t-butyl-$\eta^5$-cyclopentadienyl)-1,2-ethanediyltitanium butadiene; (cyclododecylamido)(t-butyl-$\eta^5$-cyclopentadienyl)-1,2-ethanediyltitanium 2,3-dimethylbutadiene; (cyclododecylamido)(t-butyl-$\eta^5$-cyclopentadienyl)-1,2-ethanediyltitanium isoprene; (cyclododecylamido)(t-butyl-$\eta^5$-cyclopentadienyl)-1,2-ethanediyltitanium 2,3-bis(trimethylsilyl)butadiene; (cyclododecylamido)(t-butyl-$\eta^5$-cyclopentadienyl)-1,2-ethanediyltitanium 2,3-diphenylbutadiene; (phenyl phosphido)(t-butyl-$\eta^5$-cyclopentadienyl)-1,2-ethanediyltitanium butadiene; (phenylphosphido)(t-butyl-$\eta^5$-cyclopentadienyl)-1,2-ethanediyltitanium 2,3-dimethylbutadiene; (phenylphosphido)(t-butyl-$\eta^5$-cyclopentadienyl)-1,2-ethanediyltitanium isoprene; (phenylphosphido)(t-butyl-$\eta^5$-cyclopentadienyl)-1,2-ethanediyltitanium 2,3-bis(trimethylsilyl)butadiene; (phenylphosphido)(t-butyl-$\eta^5$-cyclopentadienyl)-1,2-ethanediyltitanium 2,3-diphenylbutadiene;

(tert-butylamido)(indenyl)-1,2-ethanediyltitanium butadiene; (tertbutylamido)(indenyl)- 1,2-ethanediyltitanium 2,3-dimethylbutadiene; (tertbutylamido)(indenyl)- 1,2-ethanediyltitanium isoprene; (tertbutylamido)(indenyl)-1,2-ethanediyltitanium 2,3-bis(trimethylsilyl)butadiene; (tert-butylamido)(indenyl)-1,2-ethanediyltitanium 2,3-diphenytbutadiene; (methylamido)(indenyl)-1,2-ethanediyltitanium butadiene; (methylamido)(indenyl)-1,2-ethanediyltitanium 2,3-dimethylbutadiene; (methylamido)(indenyl)-1,2-ethanediyltitanium isoprene; (methylamido)(indenyl)-1,2-ethanediyltitanium 2,3-bis(trimethylsilyl)butadiene; (methylamido)(indenyl)-1,2-ethanediyltitanium 2,3-diphenylbutadiene; (phenylamido)(indenyl)-1,2-ethanediyltitanium butadiene; (phenylamido)(indenyl)-1,2-ethanediyltitanium 2,3-dimethylbutadiene; (phenylamido)(indenyl)-1,2-ethanediyltitanium isoprene; (phenylamido)(indenyl)-1,2-ethanediyltitanium 2,3-bis(trimethylsilyl)butadiene; (phenylamido)(indenyl)-1,2-ethanediyltitanium 2,3-diphenylbutadiene; (cyclododecylamido)(indenyl)-1,2-ethanediyltitanium butadiene; (cyclododecylamido)(indenyl)-1,2-ethanediyltitanium 2,3-dimethylbutadiene; (cyclododecylamido)(indenyl)-1,2-ethanediyltitanium isoprene; (cyclododecylamido)(indenyl)-1,2-ethanediyltitanium 2,3-bis(trimethylsilyl)butadiene; (cyclododecylamido)(indenyl)-1,2-ethanediyltitanium 2,3-diphenylbutadiene; (phenylphosphido)(indenyl)-1,2-ethanediyltitanium butadiene; (phenylphosphido)(indenyl)-1,2-ethanediyltitanium 2,3-dimethylbutadiene; (phenylphosphido)(indenyl)-1,2-ethanediyltitanium isoprene; (phenylphosphido)(indenyl)-1,2-ethanediyltitanium 2,3-bis(trimethylsilyl)butadiene; (phenylphosphido)(indenyl)-1,2-ethanediyltitanium 2,3-diphenytbutadiene;

(tert-butylamido)(tetrahydroindenyl)-1,2-ethanediyltitanium butadiene; (tertbutylamido)(tetrahydroindenyl)-1,2-ethanediyltitanium 2,3 -dimethylbutadiene; (tert-butylamido)(tetrahydroindenyl)-1,2-ethanediyltitanium isoprene; (tert-butylamido)(tetrahydroindenyl)-1,2-ethanediyltitanium 2,3-bis(trimethylsilyl)butadiene; (tertbutylamido)(tetrahydroindenyl)- 1,2-ethanediyltitanium 2,3-diphenylbutadiene; (methylamido)(tetrahydroindenyl)-1,2-ethanediyltitanium butadiene; (methylamido)(tetrahydroindenyl)-1,2-ethanediyltitanium 2,3 -dimethylbutadiene; (methylamido)(tetrahydroindenyl)-1,2-ethanediyltitanium isoprene; (methylamido)(tetrahydroindenyl)-1,2-ethanediyltitanium 2,3 -bis(trimethylsilyl)butadiene; (methylamido)(tetrahydroindenyl)-1,2-ethanediyltitanium 2,3-diphenylbutadiene; (phenylamido)(tetrahydroindenyl)-1,2-ethanediyltitanium butadiene; (phenylamido)(tetrahydroindenyl)-1,2-ethanediyltitanium 2,3 -dimethylbutadiene; (phenylamido)(tetrahydroindenyl)-1,2-ethanediyltitanium isoprene; (phenylamido)(tetrahydroindenyl)-1,2-ethanediyltitanium 2,3 -bis(trimethylsilyl)butadiene; (phenylamido)(tetrahydroindenyl)-1,2-ethanediyltitanium 2,3-diphenytbutadiene; (cyclododecylamido)(tetrahydroindenyl)-1,2-ethanediyltitanium butadiene; (cyclododecylamido)(tetrahydroindenyl)-1,2-ethanediyltitanium 2,3 -dimethylbutadiene; (cyclododecylamido)(tetrahydroindenyl)-1,2-ethanediyltitanium isoprene; (cyclododecylamido)(tetrahydroindenyl)-1,2-ethanediyltitanium 2,3-bis(trimethylsilyl)butadiene; (cyclododecylamido)(tetrahydroindenyl)-1,2-ethanediyltitanium 2,3-diphenylbutadiene; (phenylphosphido)(tetrahydroindenyl)-1,2-ethanediyltitanium butadiene; (phenylphosphido)(tetrahydroindenyl)-1,2-ethanediyltitanium 2,3 -dimethylbutadiene; (phenylphosphido)(tetrahydroindenyl)-1,2-ethanediyltitanium isoprene; (phenylphosphido)(tetrahydroindenyl)-1,2-ethanediyltitanium 2,3-bis(trimethylsilyl)butadiene; (phenylphosphido)(tetrahydroindenyl)- 1,2-ethanediyltitanium 2,3-diphenylbutadiene;

(tert-butylamido)(fluorenyl)-1,2-ethanediyltitanium butadiene; (tertbutylamido)(fluorenyl)- 1,2-ethanediyltitanium 2,3-dimethylbutadiene; (tertbutylamido)(fluorenyl)- 1,2-ethanediyltitanium isoprene; (tertbutylamido)(fluorenyl)-1,2-ethanediyltitanium 2,3 -bis(trimethylsilyl)butadiene; (tert-butylamido)(fluorenyl)-1,2-ethanediyltitanium 2,3-diphenytbutadiene; (methylamido)(fluorenyl)-1,2-ethanediyltitanium butadiene; (methylamido)(fluorenyl)-1,2-ethanediyltitanium 2,3-dimethylbutadiene; (methylamido)(fluorenyl)-1,2-ethanediyltitanium isoprene; (methylamido)(fluorenyl)-1,2-ethanediyltitanium 2,3 -bis(trimethylsilyl)butadiene; (methylamido)(fluorenyl)-1,2-ethanediyltitanium 2,3-diphenylbutadiene; (phenylamido)(fluorenyl)-1,2-ethanediyltitanium butadiene; (phenylamido)(fluorenyl)-1,2-ethanediyltitanium 2,3-dimethylbutadiene; (phenylamido)(fluorenyl)-1,2-ethanediyltitanium isoprene; (phenylamido)(fluorenyl)-1,2-ethanediyltitanium 2,3 -bis(trimethylsilyl)butadiene; (phenylamido)(fluorenyl)-1,2-ethanediyltitanium 2,3-diphenylbutadiene; (cyclododecylamido)(fluorenyl)-1,2-ethanediyltitanium butadiene; (cyclododecylamido)(fluorenyl)-1,2-ethanediyltitanium 2,3-dimethylbutadiene; (cyclododecylamido)(fluorenyl)-1,2-ethanediyltitanium isoprene; (cyclododecylamido)(fluorenyl)-1,2-ethanediyltitanium 2,3 -bis(trimethylsilyl)butadiene; (cyclododecylamido)(fluorenyl)-1,2 -ethanediyltitanium 2,3-diphenytbutadiene; (phenylphosphido)(fluorenyl)-1,2-ethanediyltitanium butadiene; (phenylphosphido)(fluorenyl)-1,2-ethanediyltitanium 2,3-dimethylbutadiene; (phenylphosphido)(fluorenyl)-1,2-ethanediyltitanium isoprene; (phenylphosphido)(fluorenyl)-1,2-ethanediyltitanium 2,3 -bis(trimethylsilyl)butadiene; (phenylphosphido)(fluorenyl)-1,2-ethanediyltitanium 2,3-diphenylbutadiene;

(tert-butylamido)(octahydrofluorenyl)-1,2-ethanediyltitanium butadiene; (tert-butylamido)(octahydrofluorenyl)-1,2-ethanediyltitanium 2,3 -dimethylbutadiene; (tert-butylamido)(octahydrofluorenyl)-1,2-ethanediyltitanium isoprene; (tert-butylamido)(octahydrofluorenyl)-1,2-ethanediyltitanium 2,3-bis(trimethylsilyl)butadiene; (tert-butylamido)(octahydrofluorenyl)- 1,2-ethanediyltitanium 2,3-diphenylbutadiene; (methylamido)(octahydrofluorenyl)-1,2-ethanediyltitanium butadiene; (methylamido)(octahydrofluorenyl)-1,2-ethanediyltitanium 2,3 -dimethylbutadiene; (methylamido)(octahydrofluorenyl)-1,2-ethanediyltitanium isoprene; (methylamido)(octahydrofluorenyl)-1,2-ethanediyltitanium 2,3-bis(trimethylsilyl)butadiene; (methylamido)(octahydrofluorenyl)-1,2ethanediyltitanium 2,3-diphenylbutadiene; (phenytamido)(octahydrofluorenyl)-1,2-ethanediyltitanium butadiene: (phenylamido)(octahydrofluorenyl)-1,2-ethanediyltitanium 2,3 -dimethylbutadiene; (phenytamido)(octahydrofluorenyl)-1,2-ethanediyltitanium isoprene; (phenytamido)(octahydrofluorenyl)-1,2-ethanediyltitanium 2,3-bis(trimethylsilyl)butadiene; (phenylamido)(octahydrofluorenyl)-1,2 -ethanediyltitanium 2,3-diphenylbutadiene; (cyclododecylamido)(octahydrofluorenyl)-1,2-ethanediyltitanium butadiene; (cyclododecylamido)(octahydrofluorenyl)-1,2-ethanediyltitanium 2,3 -dimethylbutadiene; (cyclododecylamido)(octahydrofluorenyl)-1,2-ethanediyltitanium isoprene; (cyclododecylamido)(octahydrofluorenyl)-1,2-ethanediyltitanium 2,3-bis(trimethylsilyl)butadiene; (cyclododecylamido)(octahydrofluorenyl)-1,2-ethanediyltitanium 2,3-diphenylbutadiene; (phenylphosphido)(octahydrofluorenyl)-1,2-ethanediyltitanium butadiene; (phenylphosphido)(octahydrofluorenyl)-1,2-ethanediyltitanium 2,3 -dimethylbutadiene; (phenylphosphido)(octahydrofluorenyl)-1,2-ethanediyltitanium isoprene; (phenylphosphido)(octahydrofluorenyl)-1,2-ethanediyltitanium 2,3-bis(trimethylsilyl)butadiene; (phenylphosphido)(octahydrofluorenyl)-1,2-ethanediyltitanium 2,3-diphenytbutadiene;

(tert-butylamido)($\eta^5$-cyclopentadienyl)dimethylsilanetitanium butadiene; (tert-butylamido)($\eta^5$-cyclopentadienyl)dimethylsilanetitanium 2,3 -dimethylbutadiene; (tert-butylamido)($\eta^5$-cyclopentadienyl)dimethylsilanetitanium isoprene; (tert-butylamido)($\eta^5$-cyclopentadienyl)dimethylsilanetitanium 2,3-bis(trimethylsilyl)butadiene; (tert-butylamido)($\eta^5$-cyclopentadienyl)dimethylsilanetitanium 2,3-diphenylbutadiene; (methylamido)($\eta^5$-cyclopentadienyl)dimethylsilanetitanium butadiene; (methylamido)($\eta^5$-cyclopentadienyl)dimethylsilanetitanium 2,3 -dimethylbutadiene; (methylamido)($\eta^5$-cyclopentadienyl)dimethylsilanetitanium isoprene; (methylamido)($\eta^5$-cyclopentadienyl)dimethylsilanetitanium 2,3-bis(trimethylsilyl)butadiene; (methylamido)($\eta^5$-cyclopentadienyl)dimethylsilanetitanium 2,3-diphenylbutadiene; (phenylamido)($\eta^5$-cyclopentadienyl)dimethylsilanetitanium butadiene; (phenylamido)($\eta^5$-cyclopentadienyl)dimethylsilanetitanium 2,3 -dimethylbutadiene; (phenylamido)($\eta^5$-cyclopentadienyl)dimethylsilanetitanium isoprene; (phenylamido)($\eta^5$-cyclopentadienyl)dimethylsilanetitanium 2,3-bis(trimethylsilyl)butadiene; (phenylamido)($\eta^5$-cyclopentadienyl)dimethylsilanetitanium 2,3-diphenylbutadiene; (cyclododecylamido)($\eta^5$-cyclopentadienyl)dimethylsilanetitanium butadiene; (cyclododecylamido)($\eta^5$-cyclopentadienyl)dimethylsilanetitanium 2,3 -dimethylbutadiene; (cyclododecylamido)($\eta^5$-cyclopentadienyl)dimethylsilanetitanium isoprene; (cyclododecylamido)($\eta^5$-cyclopentadienyl)dimethylsilanetitanium 2,3-bis(trimethylsilyl)butadiene; (cyclododecylamido)($\eta^5$-cyclopentadienyl)dimethylsilanetitanium 2,3-diphenylbutadiene; (phenylphosphido)($\eta^5$-cyclopentadienyl)dimethylsilanetitanium butadiene; (phenylphosphido)($\eta^5$-cyclopentadienyl)dimethylsilanetitanium 2,3 -dimethylbutadiene; (phenylphosphido)($\eta^5$-cyclopentadienyl)dimethylsilanetitanium isoprene; (phenylphosphido)($\eta^5$-cyclopentadienyl)dimethylsilanetitanium 2,3-bis(trimethylsilyl)butadiene; (phenylphosphido)($\eta^5$-cyclopentadienyl)dimethylsilanetitanium 2,3-diphenylbutadiene;

(tert-butylamido)(tetramethyl-$\eta^5$-cyclopentadienyl)dimethylsilanetitanium butadiene; (tert-butylamido)(tetramethyl-$\eta^5$-cyclopentadienyl)dimethylsilanetitanium 2,3-dimethylbutadiene; (tertbutylamido)(tetramethyl-$\eta^5$-cyclopentadienyl)dimethylsilanetitanium isoprene; (tert-butylamido)(tetramethyl-$\eta^5$-cyclopentadienyl)dimethylsilanetitanium 2,3-bis(trimethylsilyl)butadiene; (tert-butylamido)(tetramethyl-$\eta^5$-cyclopentadienyl)dimethylsilanetitanium 2,3-diphenylbutadiene; (methylamido)(tetramethyl-$\eta^5$-cyclopentadienyl)dimethylsilanetitanium butadiene; (methylamido)(tetramethyl-$\eta^5$-cyclopentadienyl)dimethylsilanetitanium 2,3-dimethylbutadiene; (methylamido)(tetramethyl-$\eta^5$-cyclopentadienyl)dimethylsilanetitanium isoprene; (methylamido)(tetramethyl-$\eta^5$-cyclopentadienyl)dimethylsilanetitanium 2,3-bis(trimethylsilyl)butadiene; (methylamido)(tetramethyl-$\eta^5$-cyclopentadienyl)dimethylsilanetitanium 2,3-diphenylbutadiene; (phenylamido)(tetramethyl-$\eta^5$-cyclopentadienyl)dimethylsilanetitanium butadiene; (phenylamido)(tetramethyl-$\eta^5$-cyclopentadienyl)dimethylsilanetitanium 2,3-dimethylbutadiene; (phenylamido)(tetramethyl-$\eta^5$-cyclopentadienyl)dimethylsilanetitanium isoprene; (phenylamido)(tetramethyl-$\eta^5$-cyclopentadienyl)dimethylsilanetitanium 2,3-bis(trimethylsilyl)butadiene; (phenylamido)(tetramethyl-$\eta^5$-cyclopentadienyl)dimethylsilanetitanium 2,3-diphenylbutadiene; (cyclododecylamido)(tetramethyl-$\eta^5$-cyclopentadienyl)dimethylsilanetitanium butadiene; (cyclododecylamido)(tetramethyl-$\eta^5$-cyclopentadienyl)dimethylsilanetitanium 2,3-dimethylbutadiene; (cyclododecylamido)(tetramethyl-$\eta^5$-cyclopentadienyl)dimethylsilanetitanium isoprene; (cyclododecylamido)(tetramethyl-$\eta^5$-cyclopentadienyl)dimethylsilanetitanium 2,3-bis(trimethylsilyl)butadiene; (cyclododecylamido)(tetramethyl-$\eta^5$-cyclopentadienyl)dimethylsilanetitanium 2,3-diphenytbutadiene; (phenylphosphido)(tetramethyl-$\eta^5$-cyclopentadienyl)dimethylsilanetitanium butadiene; (phenylphosphido)(tetramethyl-$\eta^5$-cyclopentadienyl)dimethylsilanetitanium 2,3-dimethylbutadiene; (phenylphosphido)(tetramethyl-$\eta^5$-cyclopentadienyl)dimethylsilanetitanium isoprene; (phenylphosphido)(tetramethyl-$\eta^5$-cyclopentadienyl)dimethylsilanetitanium 2,3-bis(trimethylsilyl)butadiene; (phenylphosphido)(tetramethyl-$\eta^5$-cyclopentadienyl)dimethylsilanetitanium 2,3-diphenylbutadiene;

(tert-butylamido)(t-butyl-$\eta^5$-cyclopentadienyl)dimethylsilanetitanium butadiene; (tert-butylamido)(t-butyl-$\eta^5$-cyclopentadienyl)dimethylsilanetitanium 2,3-dimethylbutadiene; (tertbutylamido)(t-butyl-$\eta^5$-cyclopentadienyl)dimethylsilanetitanium isoprene; (tert-butylamido)(t-butyl-$\eta^5$-cyclopentadienyl)dimethylsilanetitanium 2,3 -bis(trimethylsilyl)butadiene; (tert-butylamido)(t-butyl-$\eta^5$-cyclopentadienyl)dimethylsilanetitanium 2,3-diphenylbutadiene; (methylamido)(t-butyl-$\eta^5$-cyclopentadienyl)dimethylsilanetitanium butadiene; (methylamido)(t-butyl-$\eta^5$-cyclopentadienyl)dimethylsilanetitanium 2,3 -dimethylbutadiene; (methylamido)(t-butyl-$\eta^5$-cyclopentadienyl)dimethylsilanetitanium isoprene; (methylamido)(t-butyl-$\eta^5$-cyclopentadienyl)dimethylsilanetitanium 2,3-bis(trimethylsilyl)butadiene; (methylamido)(t-butyl-$\eta^5$-cyclopentadienyl)dimethylsilanetitanium 2,3 -diphenylbutadiene; (phenylamido)(t-butyl-$\eta^5$-cyclopentadienyl)dimethylsilanetitanium butadiene; (phenylamido)(t-butyl-$\eta^5$-cyclopentadienyl)dimethylsilanetitanium 2,3 -dimethylbutadiene; (phenylamido)(t-butyl-$\eta^5$-cyclopentadienyl)dimethylsilanetitanium isoprene; (phenylamido)(t-butyl-$\eta^5$-cyclopentadienyl)dimethylsilanetitanium 2,3-bis(trimethylsilyl)butadiene; (phenylamido)(t-butyl-$\eta^5$-cyclopentadienyl)dimethylsilanetitanium 2,3 -diphenylbutadiene; (cyclododecylamido)(t-butyl-$\eta^5$-cyclopentadienyl)dimethylsilanetitanium butadiene; (cyclododecylamido)(t-butyl-$\eta^5$-cyclopentadienyl)dimethylsilanetitanium 2,3-dimethylbutadiene; (cyclododecylamido)(t-butyl-$\eta^5$-cyclopentadienyl)dimethylsilanetitanium isoprene; (cyclododecylamido)(t-butyl-$\eta^5$-cyclopentadienyl)dimethylsilanetitanium 2,3- bis(trimethylsilyl)butadiene; (cyclododecylamido)(t-butyl-$\eta^5$-cyclopentadienyl)dimethylsilanetitanium 2,3-diphenylbutadiene; (phenylphosphido)(t-butyl-$\eta^5$-cyclopentadienyl)dimethylsilanetitanium butadiene; (phenylphosphido)(t-butyl-$\eta^5$-cyclopentadienyl)dimethylsilanetitanium 2,3-dimethylbutadiene; (phenylphosphido)(t-butyl-$\eta^5$-cyclopentadienyl)dimethylsilanetitanium isoprene; (phenylphosphido)(t-butyl-$\eta^5$-cyclopentadienyl)dimethylsilanetitanium 2,3-bis(trimethylsilyl)butadiene; (phenylphosphido)(t-butyl-$\eta^5$-cyclopentadienyl)dimethylsilanetitanium 2,3-diphenylbutadiene; (tert-butylamido)(indenyl)dimethylsilanetitanium butadiene; (tertbutylamido)(indenyl)dimethylsilanetitanium 2,3-dimethylbutadiene; (tertbutylamido)(indenyl)dimethylsilanetitanium isoprene; (tertbutylamido)(indenyl)dimethylsilanetitanium 2,3-bis(trimethylsilyl)butadiene; (tert-butylamido)(indenyl)dimethylsilanetitanium 2,3-diphenylbutadiene; (methylamido)(indenyl)dimethylsilanetitanium butadiene; (methylamido)(indenyl)dimethylsilanetitanium 2,3-dimethylbutadiene; (methylamido)(indenyl)dimethylsilanetitanium isoprene; (methylamido)(indenyl)dimethylsilanetitanium 2,3-bis(trimethylsilyl)butadiene; (methylamido)(indenyl)dimethylsilanetitanium 2,3-diphenylbutadiene; (phenylamido)(indenyl)dimethylsilanetitanium butadiene; (phenylamido)(indenyl)dimethylsilanetitanium 2,3-dimethylbutadiene; (phenylamido)(indenyl)dimethylsilanetitanium isoprene; (phenylamido)(indenyl)dimethylsilanetitanium 2,3-bis(trimethylsilyl)butadiene; (phenylamido)(indenyl)dimethylsilanetitanium 2,3diphenylbutadiene; (cyclododecylamido)(indenyl)dimethylsilanetitanium butadiene; (cyclododecylamido)(indenyl)dimethylsilanetitanium 2,3-dimethylbutadiene; (cyclododecylamido)(indenyl)dimethylsilanetitanium isoprene; (cyclododecylamido)(indenyl)dimethylsilanetitanium 2,3-bis(trimethylsilyl)butadiene; (cyclododecylamido)(indenyl)dimethylsilanetitanium 2,3-diphenylbutadiene; (phenylphosphido)(indenyl)dimethylsilanetitanium butadiene; (phenylphosphido)(indenyl)dimethylsilanetitanium 2,3-dimethylbutadiene; (phenylphosphido)(indenyl)dimethylsilanetitanium isoprene; (phenylphosphido)(indenyl)dimethylsilanetitanium 2,3-bis(trimethylsilyl)butadiene; (phenylphosphido)(indenyl)dimethylsilanetitanium 2,3-diphenylbutadiene; (tert-butylamido)(tetrahydroindenyl)dimethylsilanetitanium butadiene; (tertbutylamido)(tetrahydroindenyl)dimethylsilanetitanium 2,3 -dimethylbutadiene; (tert-butylamido)(tetrahydroindenyl)dimethylsilanetitanium isoprene; (tert-butylamido)(tetrahydroindenyl)dimethylsilanetitanium 2,3-bis(trimethylsilyl)butadiene; (tert-butylamido)(tetrahydroindenyl)dimethylsilanetitanium 2,3-diphenylbutadiene; (methylamido)(tetrahydroindenyl)dimethylsilanetitanium butadiene; (methylamido)(tetrahydroindenyl)dimethylsilanetitanium 2,3 -dimethylbutadiene; (methylamido)(tetrahydroindenyl)dimethylsilanetitanium isoprene; (methylamido)(tetrahydroindenyl)dimethylsilanetitanium 2,3 -bis(trimethylsilyl)butadiene; (methylamido)(tetrahydroindenyl)dimethylsilanetitanium 2,3-diphenylbutadiene; (phenylamido)(tetrahydroindenyl)dimethylsilanetitanium butadiene; (phenylamido)(tetrahydroindenyl)dimethylsilanetitanium 2,3 -dimethylbutadiene; (phenylamido)(tetrahydroindenyl)dimethylsilanetitanium isoprene; (phenylamido)(tetrahydroindenyl)dimethylsilanetitanium 2,3 -bis(trimethylsilyl)butadiene; (phenylamido)(tetrahydroindenyl)dimethylsilanetitanium 2,3-diphenylbutadiene; (cyclododecylamido)(tetrahydroindenyl)dimethylsilanetitanium butadiene; (cyclododecylamido)(tetrahydroindenyl)dimethylsilanetitanium 2,3 -dimethylbutadiene; (cyclododecylamido)(tetrahydroindenyl)dimethylsilanetitanium isoprene; (cyclododecylamido)(tetrahydroindenyl)dimethylsilanetitanium 2,3-bis(trimethylsilyl)butadiene; (cyclododecylamido)(tetrahydroindenyl)dimethylsilanetitanium 2,3-bis(trimethylsilyl)butadiene; (cyclododecylamido)(tetrahydroindenyl)dimethylsilanetitanium 2,3 -diphenylbutadiene; (phenylphosphido)(tetrahydroindenyl)dimethylsilanetitanium butadiene; (phenylphosphido)(tetrahydroindenyl)dimethylsilanetitanium 2,3 -dimethylbutadiene; (phenylphosphido)(tetrahydroindenyl)dimethylsilanetitanium isoprene; (phenylphosphido)(tetrahydroindenyl)dimethylsilanetitanium 2,3-bis(trimethylsilyl)butadiene; (phenylphosphido)(tetrahydroindenyl)dimethylsilanetitanium 2,3-diphenylbutadiene; (tert-butylamido)(fluorenyl)dimethylsilanetitanium butadiene; (tertbutylamido)(fluorenyl)dimethylsilanetitanium 2,3-dimethylbutadiene; (tertbutylamido)(fluorenyl)dimethylsilanetitanium isoprene; (tertbutylamido)(fluorenyl)dimethylsilanetitanium 2,3-bis(trimethylsilyl)butadiene; (methylamido)(fluorenyl)dimethylsilanetitanium butadiene; (methylamido)(fluorenyl)dimethylsilanetitanium 2,3-dimethylbutadiene; (methylamido)(fluorenyl)dimethylsilanetitanium isoprene; (methylamido)(fluorenyl)dimethylsilanetitanium 2,3 -bis(trimethylsilyl)butadiene; (methylamido)(fluorenyl)dimethylsilanetitanium 2,3-diphenylbutadiene; (phenylamido)(fluorenyl)dimethylsilanetitanium butadiene; (phenylamido)(fluorenyl)dimethylsilanetitanium 2,3-dimethylbutadiene; (phenylamido)(fluorenyl)dimethylsilanetitanium isoprene; (phenylamido)(fluorenyl)dimethylsilanetitanium 2,3 -bis(trimethylsilyl)butadiene; (phenylamido)(fluorenyl)dimethylsilanetitanium 2,3-diphenylbutadiene; (cyclododecylamido)(fluorenyl)dimethylsilanetitanium butadiene; (cyclododecylamido)(fluorenyl)dimethylsilanetitanium 2,3-dimethylbutadiene; (cyclododecylamido)(fluorenyl)dimethylsilanetitanium isoprene; (cyclododecylamido)(fluorenyl)dimethylsilanetitanium 2,3 -bis(trimethylsilyl)butadiene; (cyclododecylamido)(fluorenyl)dimethylsilanetitanium 2,3-diphenylbutadiene; (phenylphosphido)(fluorenyl)dimethylsilanetitanium butadiene; (phenylphosphido)(fluorenyl)dimethylsilanetitanium 2,3-dimethylbutadiene; (phenylphosphido)(fluorenyl)dimethylsilanetitanium isoprene; (phenylphosphido)(fluorenyl)dimethylsilanetitanium 2,3 -bis(trimethylsilyl)butadiene; (phenylphosphido)(fluorenyl)dimethylsilanetitanium 2,3-diphenylbutadiene; (tert-butylamido)(octahydrofluorenyl)dimethylsilanetitanium butadiene; (tertbutylamido)(octahydrofluorenyl)dimethylsilanetitanium 2,3 -dimethylbutadiene; (tert-butylamido)(octahydrofluorenyl)dimethylsilanetitanium isoprene; (tert-butylamido)(octahydrofluorenyl)dimethylsilanetitanium 2,3-bis(trimethylsilyl)butadiene; (tert-butylamido)(octahydrofluorenyl)dimethylsilanetitanium 2,3-diphenylbutadiene;

(methylamido)(octahydrofluorenyl)dimethylsilanetitanium butadiene; (methylamido)(octahydrofluorenyl)dimethylsilanetitanium 2,3-dimethylbutadiene;
(methylamido)(octahydrofluorenyl)dimethylsilanetitanium isoprene; (methylamido)(octahydrofluorenyl)dimethylsilanetitanium 2,3-bis(trimethylsilyl)butadiene;
(methylamido)(octahydrofluorenyl)dimethylsilanetitanium 2,3-diphenylbutadiene; (phenylamido)(octahydrofluorenyl)dimethylsilanetitanium butadiene; (phenylamido)(octahydrofluorenyl)dimethylsilanetitanium 2,3-dimethylbutadiene; (phenylamido)(octahydrofluorenyl)dimethylsilanetitanium isoprene; (phenylamido)(octahydrofluorenyl)dimethylsilanetitanium 2,3-bis(trimethylsilyl)butadiene;phenylamido)(octahydrofluorenyl)dimethylsilanetitanium 2,3-diphenylbutadiene; (cyclododecylamido)(octahydrofluorenyl)dimethylsilanetitanium butadiene; (cyclododecylamido)(octahydrofluorenyl)dimethylsilanetitanium 2,3-dimethylbutadiene; (cyclododecylamido)(octahydrofluorenyl)dimethylsilanetitanium isoprene; (cyclododecylamido)(octahydrofluorenyl)dimethylsilanetitanium 2,3-bis(trimethylsilyl)butadiene; (cyclododecylamido)(octahydrofluorenyl)dimethylsilanetitanium 2,3-diphenylbutadiene; (phenylphosphido)(octahydrofluorenyl)dimethylsilanetitanium butadiene; (phenylphosphido)(octahydrofluorenyl)dimethylsilanetitanium 2,3-dimethylbutadiene;
(phenylphosphido)(octahydrofluorenyl)dimethylsilanetitanium isoprene; (phenylphosphido)(octahydrofluorenyl)dimethylsilanetitanium 2,3-bis(trimethylsilyl)butadiene; and
(phenylphosphido)(octahydrofluorenyl)dimethylsilanetitanium 2,3-diphenylbutadiene.

The skilled artisan will recognize that additional members of the foregoing list will include the corresponding zirconium or hafnium containing derivatives wherein said diene forms a σ-complex as defined herein with the metal, as well as complexes that are variously substituted as herein defined.

In general, the complexes can be prepared by combining the previously mentioned reagents in an inert, organic liquid at a temperature from −100° C. to 300° C., preferably from −78 to 150° C., most preferably from 0° to 125° C. and optionally recovering the complex. Preferred alkali metal- or alkaline earth metal compounds are alkali metal alkyl compound, especially $C_{1-4}$ alkyl lithium compounds.

Suitable reaction media for the formation of the complexes are aliphatic and aromatic hydrocarbons and halohydrocarbons, ethers, and cyclic ethers. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; chlorinated-, fluorinated- or chlorofluoronated- hydrocarbons such as chlorobenzene, dichlorobenzene, and perfluorinated $C_{4-10}$ alkanes; aromatic and hydrocarbyl-substituted aromatic compounds such as benzene, toluene, xylene, and styrene, alkyl ethers having from 1 to 4 carbons in each alkyl group; $C_{1-4}$ dialkyl ether derivatives of (poly)alkylene glycols, and tetrahydrofuran. Mixtures of the foregoing are also suitable. Preferred solvents include $C_{5-10}$ alkanes and mixtures thereof. Solvated adducts of the metal complex may also be used if desired.

Examples of solvated adducts include pyridine-, diethyl-ether-, tetrahydrofuran- (THF), 1,2-dimethoxyethane-(DME), or tetramethylethylenediamine-(TMEDA) containing adducts.

The conjugated diene σ-complexes according to the present invention are surprisingly stable and readily synthesized in high yields. They are rendered catalytically active by combination with an activating cocatalyst or by use of an activating technique. Suitable activating cocatalysts for use is herein include polymeric or oligomeric alumoxanes, especially methylalumoxane, triisobutyl aluminum modified methylalumoxane, or diisobutylalumoxane; neutral Lewis acids, such as, $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl)borane; nonpolymeric, compatible, noncoordinating, ion forming compounds (including the use of such compounds under oxidizing conditions); bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. A 5,153,157, U.S. Pat. No. A 5,064,802, EP-A-468,651 (equivalent to U.S. Ser. No. 07/547,718), EP-A-520,732 (equivalent to U.S. Ser. No. 07/876,268), and WO US93/23,412 (equivalent to U.S. Ser. No. 07/884,966 filed May 1, 1992 now U.S. Pat. No. 5,350,723), the teachings of which are hereby incorporated by reference.

Combinations of neutral Lewis acids, especially the combination of a trialkyl aluminum compound having from 1 to 4 carbons in each alkyl group and a halogenated tri(hydrocarbyl)boron compound having from 1 to 10 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts.

The technique of bulk electrolysis involves the electrochemical oxidation of the metal complex under electrolysis conditions in the presence of a supporting electrolyte comprising a noncoordinating, inert anion. In the technique, solvents, supporting electrolytes and electrolytic potentials for the electrolysis are used such that electrolysis byproducts that would render the metal complex catalytically inactive are not substantially formed during the reaction. More particularly, suitable solvents are materials that are: liquids under the conditions of the electrolysis (generally temperatures from 0 to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Preferred solvents include difluorobenzene (all isomers), DME, and mixtures thereof.

The electrolysis may be conducted in a standard electrolytic cell containing an anode and cathode (also referred to as the working electrode and counter electrode respectively). Suitably materials of construction for the cell are glass, plastic, ceramic and glass coated metal. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and supporting electrolyte. The desired voltage may be determined by theoretical calculations or experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts comprising a cation and an inert, compatible, noncoordinating anion, $A^-$. Preferred supporting electrolytes are salts corresponding to the formula $G^+A^-$; wherein:

$G^+$ is a cation which is nonreactive towards the starting and resulting complex, and $A^-$ is a noncoordinating, compatible anion.

Examples of cations, $G^+$, include tetrahydrocarbyl substituted ammonium or phosphonium cations having up to 40 nonhydrogen atoms. A preferred cation is the tetra-n-butylammonium cation.

During activation of the complexes of the present invention by bulk electrolysis the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes are tetrahydrocarbylammonium salts of tetrakis(perfluoro-aryl) borates having from 1 to 10 carbons in each hydrocarbyl group, especially tetra-n-butylammonium tetrakis(pentafluorophenyl) borate.

Suitable ion forming compounds useful as a cocatalyst in one embodiment of the present invention comprise a cation which is a Bronsted acid capable of donating a proton, and an inert, compatible, noncoordinating, anion, $A^-$. Preferred anions are those containing a single coordination complex comprising a charge-bearing metal or metalloid core which anion is capable of balancing the charge of the active catalyst species (the metal cation) which is formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$(L^*—H)_d (A^{d-})$ wherein:

$L^*$ is a neutral Lewis base;

$(L^*—H)^+$ is a Bronsted acid;

$A^{d-}$ is a noncoordinating, compatible anion having a charge of d–, and d is an integer from 1 to 3.

More preferably $A^{d-}$ corresponds to the formula: $[M'^{k+} Q_3]^{d+}$ wherein:

k is an integer from 1 to 3;

n is an integer from 2 to 6;

n−k=d;

M' is an element selected from Group 13 of the Periodic Table of the Elements; and Q independently each occurrence is selected from hydride, dialkylamido, halide, alkoxide, aryloxide, hydrocarbyl, and halosubstituted-hydrocarbyl radicals (including perhalogenated hydrocarbyl radicals), said Q having up to 20 carbons with the proviso that in not more than one occurrence is Q halide. In a more preferred embodiment, d is one, ie. the counter ion has a single negative charge and corresponds to the formula $A^-$. Activating cocatalysts comprising boron which are particularly useful in the preparation of catalysts of this invention may be represented by the following general formula:

$[L^*—H]^+[BQ_4]$ wherein:

$L^*$ is as previously defined;

B is boron; and

Q is a fluorinated $C_{1-20}$ hydrocarbyl group.

Most preferably, Q is each occurrence a fluorinated aryl group, especially, a pentafluorophenyl group.

Illustrative, but not limiting, examples of boron compounds which may be used as an activating cocatalyst in the preparation of the improved catalysts of this invention are tri-substituted ammonium salts such as:

trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl) borate, tri(n-butyl)ammonium tetrakis(pentafluorophenyl) borate, tri(secbutyl)ammonium tetrakis(pentafluorophenyl) borate, N,N-dimethylanilinium tetrakis(pentafluorophenyl) borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenylborate, triethylammonium tetrakis-(2,3,4,6-tetrafluorophenyl) borate, tripropylammonium tetrakis-(2,3,4,6-tetrafluorophenyl) borate, tri(n-butyl)ammonium tetrakis-(2,3,4,6-tetrafluorophenyl) borate, dimethyl(t-butyl)ammonium tetrakis-(2,3,4,6-tetrafluorophenyl) borate, N,N-dimethylanilinium tetrakis-(2,3,4,6-tetrafluorophenyl) borate, N,N-diethylanilinium tetrakis-(2,3,4,6-tetrafluorophenyl) borate, and N,N-dimethyl-(2,4,6-trimethylanilinium) tetrakis-(2,3,4,6-tetrafluorophenyl) borate;

dialkyl ammonium salts such as:

di-(i-propyl)ammonium tetrakis(pentafluorophenyl) borate, and dicyclohexylammonium tetrakis(pentafluorophenyl) borate; and tri-substituted phosphonium salts such as: triphenylphospnonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate.

Preferred [L*—H]$^+$ cations are N,N-dimethylanilinium and tributylammonium.

Another suitable ion forming, activating cocatalyst comprises a salt of a cationic oxidizing agent and a noncoordinating, compatible anion represented by the formula:

$$(OX^{e+})_d(A^{d-})_e$$

wherein:

$Ox^{e+}$ is a cationic oxidizing agent having a charge of e+;

e is an integer from 1 to 3; and $A^{d-}$, and d are as previously defined.

Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activating cocatalysts, especially tetrakis(pentafluorophenyl)borate.

Another suitable ion forming, activating cocatalyst comprises a compound which is a salt of a carbenium ion and a noncoordinating, compatible anion represented by the formula:

$$©+A^-$$

wherein:

©+ is a $C_{1-20}$ carbenium ion; and $A^-$ is as previously defined. A preferred carbenium ion is the trityl cation, i.e. triphenylcarbenium.

The foregoing activating technique and ion forming cocatalysts are also preferably used in combination with a tri(hydrocarbyl)aluminum compound having from 1 to 4 carbons in each hydrocarbyl group, an oligomeric or polymeric alumoxane compound, or a mixture of a tri(hydrocarbyl)aluminum compound having from 1 to 4 carbons in each hydrocarbyl group and a polymeric or oligomeric alumoxane.

The molar ratio of catalyst/cocatalyst employed preferably ranges from 1:10,000 to 100:1, more preferably from 1:5000 to 10:1, most preferably from 1:10 to 1:1. In a particularly preferred embodiment of the invention the cocatalyst can be used in combination with a tri(hydrocarbyl)aluminum compound having from 1 to 10 carbons in each hydrocarbyl group or an oligomeric or polymeric alumoxane. Mixtures of activating cocatalysts may also be employed. It is possible to employ these aluminum compounds for their beneficial ability to scavenge impurities such as oxygen, water, and aldehydes from the polymerization mixture. Preferred aluminum compounds include trialkyl aluminum compounds having from 2 to 6 carbons in each alkyl group, especially those wherein the alkyl groups are ethyl, propyl, isopropyl, n-butyl, isobutyl, pentyl, neopentyl, or isopentyl, and methylalumoxane, modified methylalumoxane (that is, methylalumoxane modified by reaction with triisobutyl aluminum) (MMAO) and diisobutylalumoxane. The molar ratio of aluminum compound to metal complex is preferably from 1:10,000 to 1000:1, more preferably from 1:5000 to 100:1, most preferably from 1:100 to 100:1. A most preferred activating cocatalyst comprises both a strong Lewis acid and an alumoxane, especially tris(pentafluorophenyl)borane and methylalumoxane, modified methylalumoxane, or diisobutylalumoxane.

The novel zwitterionic complexes resulting from activation by combination with neutral Lewis acid activating cocatalysts in a preferred embodiment correspond to one of the two equilibrium structures of the formula:

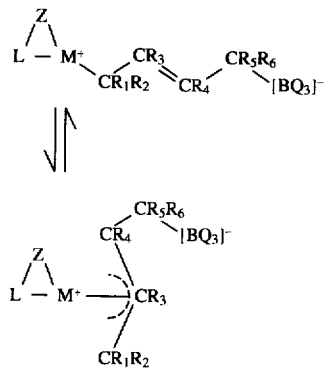

wherein:

M is a Group 4 metal in the +4 formal oxidation state;

L is a group containing a cyclic, delocalized, anionic, π-system through which the group is bound to M, and which group is also bound to Z;

Z is a moiety bound to M via a σ-bond, comprising boron, or a member of Group 14 of the Periodic Table of the Elements, and also comprising nitrogen, phosphorus, sulfur or oxygen, said moiety having up to 60 nonhydrogen atoms;

$R_1$, $R_2$, $R_3$, $R_4$, $R_5$, and $R_6$ are independently hydrogen or anionic ligand groups selected from the group consisting of hydrocarbyl, silyl and combinations thereof, said ligand group having from 1 to 20 nonhydrogen atoms;

B is boron, and

Q is as previously defined.

Further preferred zwitterionic derivatives according to the present invention are the equilibrium mixture corresponding to the formulas:

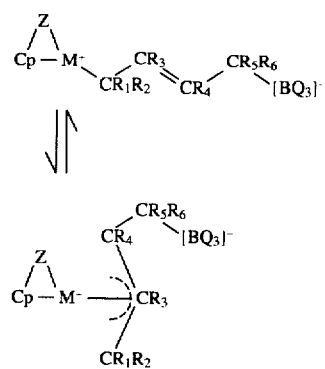

wherein

Z, and M are as previously defined;

each $R_1$, $R_2$, $R_3$, $R_4$, $R_5$, and $R_6$ is independently hydrogen or an anionic ligand group selected from the group consisting of hydrocarbyl, silyl and combinations thereof, said ligand group having from 1 to 10 nonhydrogen atoms; and Cp is a $C_5H_4$ cyclopentadienyl group bound to Z and bound in an $\eta^5$ bonding mode to M or is such an $\eta^5$ bound group substituted with from one to four substituents independently selected from hydrocarbyl, halocarbyl, silyl, germyl, halo, cyano, and combinations thereof, said substituent having up to nonhydrogen atoms, and optionally, two such substituents (except cyano or halo) together cause Cp to have a fused ring structure;

B is boron; and

Q is a fluorinated $C_{1-20}$ hydrocarbyl group.

More preferred metal coordination complexes according to the present invention correspond to the formula:

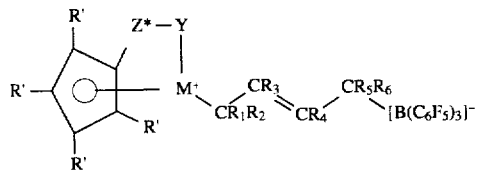

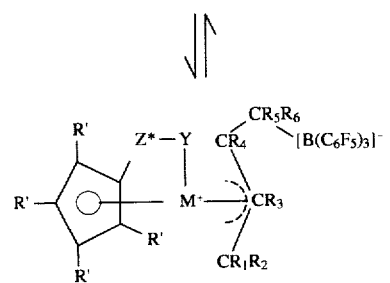

wherein:

R' each occurrence is independently selected from hydrogen, hydrocarbyl, silyl, germyl, halo, cyano, and combinations thereof, said R' having up to 20 nonhydrogen atoms, and optionally, two R' groups (where R' is not hydrogen, halo or cyano) together form a divalent derivative thereof connected to adjacent positions of the cyclopentadienyl ring to form a fused ring structure;

Y is —O—, —S—, —NR*—, —PR*—;

M is titanium or zirconium in the +4 formal oxidation state;

each $R_1$, $R_2$, $R_3$, $R_4$, $R_5$, and $R_6$ is independently selected from the group consisting of hydrogen and $C_{1-8}$ hydrocarbyl; and Z* is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$; wherein:

R* each occurrence is independently hydrogen, or a member selected from hydrocarbyl, silyl, halogenated alkyl, halogenated aryl, and combinations thereof, said R* having up to 10 nonhydrogen atoms, and optionally, two R* groups from Z* (when R* is not hydrogen), or an R* group from Z* and an R* group from Y form a ring system.

Most highly preferred are the equilibrium zwitterionic metal coordination complexes corresponding to the formula: wherein:

M is titanium;

$R_1$, $R_2$, $R_5$, and $R_6$ are hydrogen;

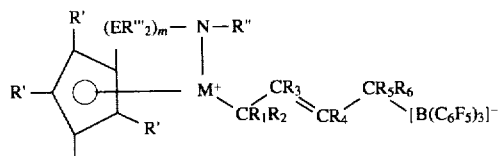

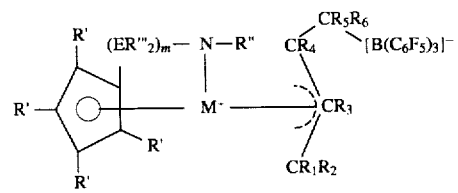

$R_3$, and $R_4$ are hydrogen, $C_{1-4}$ alkyl or phenyl;

R' each occurrence is independently selected from hydrogen, silyl, hydrocarbyl and combinations thereof, said R' having up to 10 carbon or silicon atoms, or two such R' groups on the substituted cyclopentadienyl group (when R' is not hydrogen) together form a divalent derivative thereof connected to adjacent positions of the cyclopentadienyl ring;

R" is t-butyl;

R''' is independently each occurrence hydrogen or $C_{1-10}$ hydrocarbyl;

E is independently each occurrence silicon or carbon; and m is 1 or 2.

The catalysts may be used to polymerize ethylenically and/or acetylenically unsaturated monomers having from 2 to 100 carbon atoms either alone or in combination. Preferred monomers include the $C_{2-20}$ α-olefins especially ethylene, propylene, isobutylene, 1-butene, 1-hexene, 4-methyl-1-pentene, and 1-octene and mixtures thereof. Other preferred monomers include styrene, $C_{1-4}$ alkyl substituted styrene, tetrafluoroethylene, vinylbenzocyclobutane, ethylidenenorbornene 1,4-hexadiene and mixtures thereof with ethylene.

As polymerization catalysts, the invented compositions possess higher efficiency of operation and are capable of operation at higher temperatures than corresponding catalysts based on complexes lacking in the diene ligand group. In addition the present catalysts achieve higher molecular weight polymers than the above comparative polymers. Such polymer products are capable of preparing wrapping films and molded articles having improved strength and impact properties.

In general, the polymerization may be accomplished at conditions well known in the prior art for Ziegler-Natta or Kaminsky-Sinn type polymerization reactions, i.e., temperatures from 0°–250° C. and pressures from atmospheric to 1000 atmospheres (0.1 to 100 MPa). Suspension, solution, slurry, gas phase or other process conditions may be employed if desired. A support, especially silica, modified silica (silica modified by calcining, treatment with a trialkylaluminum compound having from 1 to 10 carbons in each alkyl group, or treatment with an alkylalumoxane), alumina, or a polymer (especially polytetrafluoroethylene or a polyolefin) may be employed, and desirably is employed when the catalysts are used in a gas phase polymerization process. The support is preferably employed in an amount to provide a weight ratio of catalyst (based on metal):support from 1:100,000 to 1:10, more preferably from 1:50,000 to 1:20, and most preferably from 1:10,000 to 1:30.

In most polymerization reactions the molar ratio of catalyst: polymerizable compounds employed is from $10^{-2}:1$ to $10^{-1}:1$, more preferably from $10^{-12}:1$ to $10^{-5}:1$.

Suitable solvents for polymerization are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and aromatic and alkylsubstituted aromatic compounds such as benzene, toluene, and xylene. Suitable solvents also include liquid olefins which may act as monomers or comonomers including ethylene, propylene, 1-butene, butadiene, cyclopentene, 1-hexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), 4-vinylcyclohexene, and vinylcyclohexane. Mixtures of the foregoing are also suitable.

The catalysts may also be utilized in combination with at least one additional homogeneous or heterogeneous polymerization catalyst in separate reactors connected in series or in parallel to prepare polymer blends having desirable properties. An example of such a process is disclosed in WO 94/00500, equivalent to U.S. Ser. No. 07/904,770 now abandoned, as well as U.S. Ser. No. 08/10958, filed Jan. 29, 1993 now abandoned, the teachings or which are hereby incorporated by reference herein.

One such solution phase polymerization process comprises:

contacting in a solvent one or more α-olefins with a metal complex according to the present invention and one or more cocatalyst activators in one or more continuous stirred tank or tubular reactors connected in series or parallel, and recovering the resulting polymerizate.

In another such solution phase polymerization process, in one or more of the foregoing reactors, one or more α-olefins are also contacted with a catalyst composition comprising one or more metal complexes according to the present invention in admixture with one or more homogeneous metallocene complexes other than a complex according to the present invention, said catalyst composition also comprising one or more cocatalyst activators.

In yet another solution process an ethylene/α-olefin interpolymer composition is prepared by:

(A) contacting ethylene and at least one other α-olefin under solution polymerization conditions in the presence of a homogeneous catalyst composition comprising a metal complex of the present invention with at least one of the aforementioned activating cocatalysts in at least one reactor to produce a solution of a first interpolymer, (B) contacting ethylene and at least one other α-olefin under solution polymerization conditions and at a higher polymerization reaction temperature than used in step (A) in the presence of a heterogeneous Ziegler catalyst in at least one other reactor to produce a solution of a second interpolymer, and (C) combining the solution of the first interpolymer with the solution of the second interpolymer to form a solution comprising the ethylene/α-olefin interpolymer composition, and (D) recovering the ethylene/α-olefin interpolymer composition.

Preferably the heterogeneous Ziegler catalyst comprises:
(i) a solid support component comprising magnesium halide, silica, modified silica, alumina, aluminum phosphate, or a mixture thereof, and
(ii) a transition metal component represented by the formula:

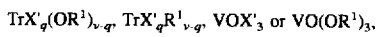

wherein:

Tr is a Group 4, 5, or 6 metal, q is a number from 0 to 6 that is less than or equal to v, v is the formal oxidation number of Tr, X' is a halogen, $R^1$ independently each occurrence is a hydrocarbyl group having from 1 to 20 carbon atoms.

These polymerizations are generally carried out under solution s conditions to facilitate the intimate mixing of the two polymer-containing streams. The foregoing technique allows for the preparation of ethylene/α-olefin interpolymer compositions having a broad range of molecular weight distribution and composition distribution. Preferably, the heterogeneous catalyst is also chosen from those catalysts which are capable of efficiently producing the polymers under high temperature, especially, temperatures greater than or equal to 180° C. under solution process conditions.

In a still further embodiment, there is provided a process for preparing an ethylene/α-olefin interpolymer composition, comprising:

(A) polymerizing ethylene and at least one other α-olefin in a is solution process under suitable solution polymerization temperatures and pressures in at least one reactor containing a catalyst composition comprising the metal complex of the present invention with at least one of the aforementioned activating cocatalysts to produce a first interpolymer solution, (B) passing the interpolymer solution of (A) into at least one other reactor containing a heterogeneous Ziegler catalyst, in the presence of ethylene and optionally one other α-olefin under solution polymerization conditions to form a solution comprising the ethylene/α-olefin interpolymer composition, and (C) recovering the ethylene/α-olefin interpolymer composition.

Preferably the heterogeneous Ziegler catalyst comprises:
(i) a solid support component comprising a magnesium halide or silica, and
(ii) a transition metal component represented by the formula: $TrX'_q(OR^1)_{v-q}$, $TrX'_qR^1_{v-q}$, $VOX'_3$ or $VO(OR^1)_3$, wherein:

Tr, X', q, v, and $R_1$ are as previously defined.

The foregoing technique also allows for the preparation of ethylene/α-olefin interpolymer compositions having a broad range of molecular weight distributions and composition distributions. Particularly desirable α-olefins for use in the foregoing processes are $C_{4-8}$ α-olefins, most desirably 1-octene.

Having described the invention the following examples are provided as further illustration thereof and are not to be construed as limiting.

Unless stated to the contrary all parts and percentages are expressed on a weight basis.

EXAMPLE 1

(A) Preparation of (t-butylamido)(tetramethyl-$\eta^5$-cyclopentadienyl) dimethylsilanetitanium (2,3-dimethyl-1,3-butadiene)

In an inert atmosphere glove box, 0.500 g (1.36 mmol) of $C_5Me_4SiMe_2NCMe_3TiCl_2$ ((t-butylamido)(tetramethyl-$\eta^5$-cyclopentadienyl)dimethylsilanetitanium dichloride) was dissolved into 50 mL of hexane. To this solution was added 1.54 ml (0.0136 mol) of 2,3-dimethyl-1,3-butadiene, followed by addition of 1.09 ml of a 2.50M hexane solution of n-butyl lithium (2.72 mmol). The color changed from yellow to dark brown. After about 60 minutes reaction time under reflux the mixture was cooled and filtered using Celite™ diatomaceous earth filter aid and 10 ml of additional hexane to clean the flask. The solvent was removed from the combined filtrates under reduced pressure giving the product as a dark colored solid. The solid was collected giving 0.508 g (98.6 percent yield) of (t-butylamido)-(tetramethyl-$\eta^5$-cyclopentadienyl)dimethyl-silanetitanium dimethyl-1,3-butadiene.

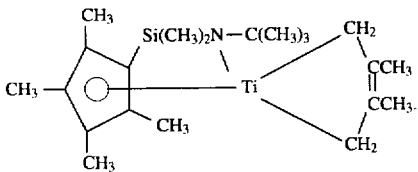

The product's identity was confirmed by $^1$H NMR spectral analysis. Characterization for (t-butylamido)(tetramethyl-$\eta^5$-cyclopentadienyl)dimethylsilanetitanium 2,3-dimethyl-1,3-butadiene ($C_6D_6$, ppm): δ2.18-(s, $C_5Me_4$,6H); 2.06 (broad d, HHC=C(CH$_3$)—C(CH$_3$)=CHH, 2H, $J_{HH}$= 8.8 Hz); 1.94 (broad s, HHC=C(CH$_3$)—C(CH$_3$)=CHH, 6H); 1.7 (broad d, HHC=C(CH$_3$)—C(CH$_3$)=CHH, 2H); 1.46 (s, $C_5Me_4$, 6H); 1.10 (s, $^t$Bu, 9H); 0.75 (s,SiMe$_2$, 6H).

Catalyst Preparation

In an inert atmosphere glove box, 0.0100 g (0.0263 mmol) of (t-butylamido)(tetramethyl-$\eta^5$-cyclopentadienyl)dimethylsilanetitanium (2,3-dimethyl-1,3-butadiene) ($C_5Me_4SiMe_2NCMe_3TiCH_2CMeCMeCH_2$) was combined with 0.0230 g of B($C_6F_5$)$_3$ (0.0449 mmol) in 1 mL of $C_6D_6$. The reaction mixture was placed in an NMR tube and the $^1$H NMR spectrum acquired. The results indicate the reaction product was a zwitterion having the two possible equilibrium forms:

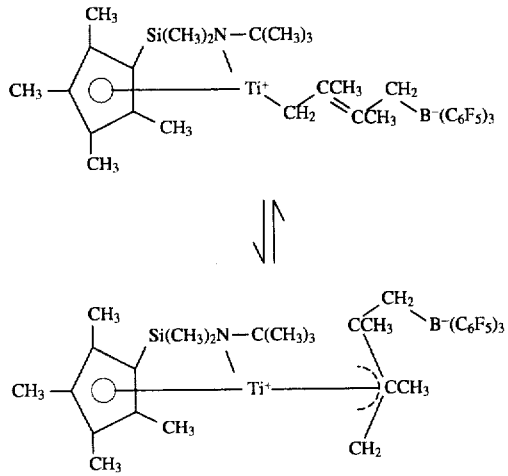

$^1$H NMR characterization: ($C_6D_6$, ppm): δ2.76 (d CHHC(CH$_3$)C(CH$_3$)—CH$_2$B(C$_6$F$_5$)$_3$; 1H, $J_{HH}$=8.4 Hz); 2.34 (d, CHHC(CH$_3$)C(CH$_3$)CH$_2$B(C$_6$F$_5$)$_3$, 1H, $J_{HH}$=8.5 Hz); 2.07, 1.44, 1.34, 1.21, 1.18, (s each, Me, total 18 H); 0.96(broad m, CH$_2$C(CH$_3$)C(CH$_3$)CHHB(C$_6$F$_5$)$_3$, 1H); 0.84 (s, $^t$Bu, 9H); 0.63, 0.46 (s each, SiMe$_2$, 3H each); 0.07 (broad m, CH$_2$C(CH$_3$)C(CH$_3$)CHHB(C$_5$F$_5$)$_3$, 1H).

Polymerization

A two-liter Parr reactor was charged with 746, g of Isopar™ E mixed alkanes solvent and 120 g of 1-octene comonomer. Hydrogen was added as a molecular weight control agent by differential pressure expansion from an about 75 mL addition tank at 25 psi (170 kPa). The reactor was heated to the polymerization temperature of 140° C. and saturated with ethylene at 500 psig (3.45 MPa). 2.0 umol each of catalyst ($C_5Me_4SiMe_2NCMe_3TiCH_2CMeCMeCH_2$) and cocatalyst (B($C_6F_5$)$_3$) (0.005M solutions in toluene) were premixed in the drybox for about 1 minute, then transferred to a catalyst addition tank and injected into the reactor. The polymerization conditions were maintained for minutes with ethylene on demand. Total reactor exotherm was 5.7° C. The resulting solution was removed from the reactor, and a hindered phenol antioxidant (Irganox™ 1010) was added. Polymers were recovered by removing solvent in a vacuum oven set at 120° C. for about 20 hours. Yield of ethylene/1-octene copolymer was 162 g (1,700,00 g polymer/g Ti). The polymer melt index (I$_2$, ASTM D-1238, Procedure A, condition E) was 2.58.

The formation of the novel zwiterion compound by combination with the above cocatalyst which reaction product is more soluble in hydrocarbon solvents than cationic metal compounds, illustrates the unexpectedly advantageous properties of the present Group 4 metal complexes.

EXAMPLE 2

In an inert atmosphere glove box, 0.500 g (1.36 mmol) of (t-butylamido)(tetramethyl-$\eta^5$-cyclopentadienyl)dimethylsilanetitanium dichloride was dissolved into approximately 50 mL of dry, degassed mixed hexanes. To this yellow solution was added 1.36 mL of isoprene (13.6 mmol) followed by 1.09 mL of $^n$BuLi (2.72 mmol, 2.5M in hexane). Addition of the alkyl lithium resulted in an immediate color change to a dark red color. The reaction mixture was refluxed for 45 to 60 minutes after which time the reaction mixture was cooled to room temperature. The hexane solution was filtered through Celite™ brand diatomaceous earth filter aid, using 10 mL of additional hexane to wash the insoluble materials. The combined hexane filtrate was taken to dryness under reduced pressure giving the product, (t-butylamido)(tetramethyl-$\eta^5$-cyclopentadienyl)dimethylsilanetitanium isoprene, as a very dark reddish purple solid in 97.6 percent yield (0.503 g). The identity of the product was confirmed by X-ray structural analysis, with the $\Delta d$ determined from the crystal structure of –0.168 Å.

The resulting X-ray structure is provided as FIG. 1.

What is claimed is:

1. A catalyst composition comprising a metal complex which is catalytically activated by combination with an activating cocatalyst or by use of an activating technique, said metal complex containing one and only one cyclic, delocalized, anionic, π-bonded group, and corresponding to the formula:

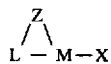

wherein:

M is a Group 4 metal in the +4 formal oxidation state;

L is a group containing a cyclic, delocalized, anionic, π-system through which the group is bound to M, and which group is also bound to Z;

Z is a moiety bound to M via a σ-bond, comprising an element selected from the group consisting of boron, and the members of Group 14 of the Periodic Table of the Elements, and also comprising an element selected from the group consisting of nitrogen, phosphorus sulfur and oxygen, said moiety having up to 60 nonhydrogen atoms; and X is a conjugated diene or a hydrocarbyl-, halocarbyl-, or silyl- substituted derivative thereof, said X having from 4 to 40 nonhydrogen atoms, and being coordinated to M so as to form a metallocyclopentene therewith.

2. A catalyst composition according to claim 1 wherein the activating cocatalyst is selected from the group consisting of polymeric or oligomeric alumoxanes, neutral Lewis acids; nonpolymeric, inert, compatible, noncoordinating, ion forming compounds; and combinations thereof.

3. A catalyst composition according to claim 1 wherein the metal complex corresponds to the formula:

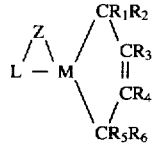

wherein:

M is titanium or zirconium in the +4 formal oxidation state;

L is a group containing a cyclic, delocalized, anionic, π-system through which the group is bound to M, and which group is also bound to Z;

Z is a moiety bound to M via a σ-bond, comprising an element selected from the group consisting of boron, and the members of Group 14 of the Periodic Table of the Elements, and also comprising an element selected from the group consisting of nitrogen, phosphorus, sulfur and oxygen, said moiety having up to 60 nonhydrogen atoms; and $R_1$, $R_2$, $R_3$, $R_4$, $R_5$, and $R_6$ are independently hydrogen or a substituent selected from the group consisting of hydrocarbyl, silyl, hydrocarbyl substituted silyl and silyl substituted hydrocarbyl, said substituent having from 1 to 20 nonhydrogen atoms.

4. A catalyst composition according to claim 3 wherein the metal complex corresponds to the formula:

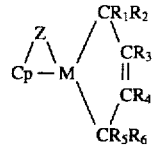

wherein

Z, and M are as previously defined in claim 3;

each $R_1$, $R_2$, $R_3$, $R_4$, $R_5$, and $R_6$ is independently hydrogen or a substituent selected from the group consisting of hydrocarbyl, silyl, hydrocarbyl substituted silyl and silyl substituted hydrocarbyl, said substituent having from 1 to 10 nonhydrogen atoms; and Cp is a $C_5H_4$ group or a substituted $C_5H_4$ group substituted with from one to four substituents independently selected from hydrocarbyl, halocarbyl, silyl, germyl, halo, cyano, hydrocarbyl substituted silyl, silyl substituted hydrocarbyl and halohydrocarbyl, said substituent having up to 20 nonhydrogen atoms, and optionally, two such substituents (except cyano or halo) together cause Cp to have a fused ring structure, said Cp being bound to Z and bound in a $\eta^5$ bonding mode to M.

5. A catalyst composition according to claim 4 wherein the metal complex corresponds to the formula:

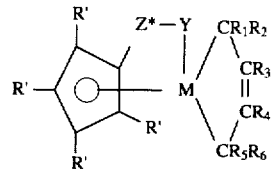

wherein:

R' each occurrence is independently selected from hydrogen, hydrocarbyl, silyl, germyl, halo, cyano, hydrocarbyl substituted silyl, silyl substituted hydrocarbyl and halohydrocarbyl, said R' having up to nonhydrogen atoms, and optionally, two R' groups (where R' is not hydrogen, halo or cyano) together form a divalent derivative thereof connected to adjacent positions of the cyclopentadienyl ring to form a fused ring structure;

Y is —O—, —S—, —NR*—, —PR*—,

M is titanium or zirconium in the +4 formal oxidation state;

each $R^1$, $R^2$, $R^3$, $R^4$, $R^5$, and $R^6$ is independently selected from the group consisting of hydrogen and $C_{1-8}$ hydrocarbyl; and Z* is SiR*$_2$, CR*$_2$, SiR*$_2$SiR*$_2$, CR*$_2$CR*$_2$, CR*=CR*, CR*$_2$SiR*$_2$, or GeR*$_2$; wherein:

R* each occurrence is independently hydrogen, or a member selected from hydrocarbyl, silyl, halogenated alkyl, and halogenated aryl, said R* having up to 10 nonhydrogen atoms, and optionally, two R* groups from Z* (when R* is not hydrogen), or an R* group from Z* and an R* group from Y form a ring system.

6. A catalyst composition according to claim 5 wherein the metal complex corresponds to the formula:

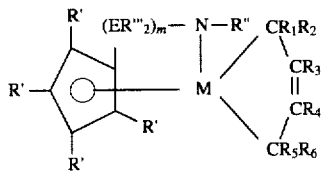

wherein:

M is titanium;

$R_1$, $R_2$, $R_5$, and $R_6$ are hydrogen;

$R_3$, and $R_4$ are hydrogen, $C_{1-4}$ alkyl or phenyl;

R' each occurrence is independently selected from hydrogen, silyl, hydrocarbyl, hydrocarbyl substituted silyl and silyl substituted hydrocarbyl, said R' having up to 10 carbon or silicon atoms, or two such R' groups on the substituted cyclopentadienyl group (when R' is not hydrogen) together form a divalent derivative thereof connected to adjacent positions of the cyclopentadienyl ring;

R" is t-butyl;

R'" is independently each occurrence hydrogen or $C_{1-10}$ hydrocarbyl;

E is independently each occurrence silicon or carbon; and m is 1 or 2.

7. A catalyst composition according to claim 1 wherein the metal complex selected from the group consisting of (tert-butylamido)(tetramethyl-$\eta^5$-cyclopentadienyl)dimethylsilanetitanium 1,3-butadiene; (tert-butylamido)(tetramethyl-$\eta^5$-cyclopentadienyl)dimethylsilanetitanium 2,3-dimethyl-1,3-butadiene; and (tert-butylamido)(tetramethyl-$\eta^5$-cyclopentadienyl)dimethylsilanetitanium isoprene.

8. A catalyst composition according to claim 1 wherein the activating cocatalyst is tris(pentafluorophenyl)borane or a combination of tris(pentafluorophenyl)borane and a polymeric or oligomeric alumoxane.

9. A zwiterionic metal complex corresponding to the formula:

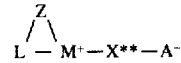

wherein:

X** is the divalent remnant of the conjugated diene, X, formed by ring opening at one of the carbon to metal bonds of the metallocyclopentene of the formula:

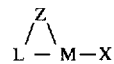

and L, Z, M and X are as defined in claim 1, and

A is the moiety derived from a neutral Lewis acid activating cocatalyst.

10. A metal complex according to claim 9 wherein $A^-$ is $B(C_6F_5)_3-$.

11. A polymerization process comprising contacting an addition polymerizable ethylenically unsaturated monomer with a catalyst under polymerization conditions characterized in that the catalyst is a composition according to claim 1.

* * * * *

UNITED STATES PATENT AND TRADEMARK OFFICE
CERTIFICATE OF CORRECTION

PATENT NO. : 5,539,068

DATED : Jul. 23, 1996

INVENTOR(S) : Devore, et al.

It is certified that error appears in the above-identified patent and that said Letters Patent is hereby corrected as shown below:

Title Page, column 1, Title, line 1, "GROUP 4," should correctly read --GROUP 4--.

Claim 2, Col. 29, line 45, "acids;" should correctly read --acids,--.

Claim 2, Col. 29, line 46, "compounds;" should correctly read --compounds,--.

Claim 5, column 30, line 48, following "to", insert therefor --20--.

Claim 7, column 32, line 2, "cyclopentadienyl)dimenthylsilanctitanium" should correctly read --cyclopentadienyl)-dimenthylsilanctitanium--.

Claim 9, column 32, line 23, "A is" should correctly read --A- is--.

Signed and Sealed this

Thirteenth Day of July, 1999

Attest:

Q. TODD DICKINSON

*Attesting Officer*   *Acting Commissioner of Patents and Trademarks*